(12) United States Patent
Gunderson et al.

(10) Patent No.: US 10,143,424 B2
(45) Date of Patent: Dec. 4, 2018

(54) DETECTION OF MEDICAL ELECTRICAL LEAD ISSUES

(71) Applicant: Medtronic, Inc., Minneapolis, MN (US)

(72) Inventors: Bruce D. Gunderson, Plymouth, MN (US); James D. Reinke, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 235 days.

(21) Appl. No.: 14/826,396

(22) Filed: Aug. 14, 2015

(65) Prior Publication Data
US 2017/0042482 A1   Feb. 16, 2017

(51) Int. Cl.
| | |
|---|---|
| *A61B 5/00* | (2006.01) |
| *A61N 1/39* | (2006.01) |
| *A61B 5/0468* | (2006.01) |
| *A61N 1/08* | (2006.01) |
| A61B 5/042 | (2006.01) |
| A61N 1/37 | (2006.01) |
| A61B 5/04 | (2006.01) |
| A61B 5/0424 | (2006.01) |
| A61B 5/0452 | (2006.01) |

(52) U.S. Cl.
CPC .......... *A61B 5/7203* (2013.01); *A61B 5/0468* (2013.01); *A61B 5/686* (2013.01); *A61B 5/6867* (2013.01); *A61N 1/08* (2013.01); *A61N 1/37* (2013.01); *A61N 1/3925* (2013.01); *A61B 5/04017* (2013.01); *A61B 5/0422* (2013.01); *A61B 5/0424* (2013.01); *A61B 5/04525* (2013.01); *A61B 2560/0276* (2013.01); *A61N 1/3706* (2013.01)

(58) Field of Classification Search
None
See application file for complete search history.

(56) References Cited

U.S. PATENT DOCUMENTS

| | | |
|---|---|---|
| 5,354,316 A | 10/1994 | Keimel |
| 5,507,782 A | 4/1996 | Kieval et al. |
| | (Continued) | |

FOREIGN PATENT DOCUMENTS

| | | |
|---|---|---|
| WO | 199736647 | 10/1997 |
| WO | 2014169145 | 10/2014 |

OTHER PUBLICATIONS (PCT/US2016/045231) PCT Notification of Transmittal of the International Search Report and the Written Opinion of the International Searching Authority, dated Oct. 5, 2016, 11 pages.
(Continued)

*Primary Examiner* — Erica Lee

(57) ABSTRACT

An implantable medical device includes a sensing module configured to receive a cardiac electrical signal via electrodes carried by a medical electrical lead coupled to the implantable medical device and a control module configured to detect a lead issue. The sensing module is configured to produce cardiac sensed event signals and spike detect signals. The control module is configured to determine event intervals defined by consecutive ones of the received cardiac sensed event signals and the received spike detect signals and identify one or more received spike detect signals as lead issue spikes based on at least one of the determined event intervals.

28 Claims, 12 Drawing Sheets

(56) References Cited

U.S. PATENT DOCUMENTS

| | | | |
|---|---|---|---|
| 5,545,186 | A | 8/1996 | Olson et al. |
| 5,910,156 | A | 6/1999 | Cinbis et al. |
| 6,393,316 | B1 | 5/2002 | Gillberg et al. |
| 7,031,771 | B2 | 4/2006 | Brown et al. |
| 7,283,863 | B2 | 10/2007 | Gunderson et al. |
| 7,289,851 | B2 | 10/2007 | Gunderson et al. |
| 8,078,277 | B2 | 12/2011 | Gunderson et al. |
| 8,160,684 | B2 | 4/2012 | Ghanem et al. |
| 8,437,842 | B2 | 5/2013 | Zhang et al. |
| 8,712,523 | B2 | 4/2014 | Sanghera et al. |
| 8,781,585 | B2 | 7/2014 | Gunderson et al. |
| 2004/0015197 | A1* | 1/2004 | Gunderson .......... A61B 5/0452 607/27 |
| 2006/0235476 | A1* | 10/2006 | Gunderson .......... A61B 5/0456 607/5 |
| 2009/0299422 | A1 | 12/2009 | Ousdigian et al. |
| 2012/0143278 | A1 | 6/2012 | Ryu et al. |
| 2013/0253352 | A1 | 9/2013 | Bomzin et al. |

OTHER PUBLICATIONS

U.S. Appl. No. 14/687,053, Reinke, et al., "Pace Pulse Detector for an Implantable Medical Device", filed Apr. 15, 2015, 63 pages.

U.S. Appl. No. 14/686,947, Reinke, et al., "Implantable Medical Device (IMD) Sensing Modifications Responsive to Detected Pacing Pulses,", filed Apr. 15, 2015, 62 pages.

* cited by examiner

DETECTION OF MEDICAL ELECTRICAL LEAD ISSUES

TECHNICAL FIELD

The disclosure relates to implantable medical devices and associated methods for detecting medical electrical lead issues.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors.

IMDs may deliver therapy to and/or monitor conditions of a variety of organs, nerves, muscle or tissue, such as the heart, brain, stomach, spinal cord, pelvic floor, or the like. Some IMDs, such as cardiac pacemakers or implantable cardioverter defibrillators (ICDs) monitor a patient's heart activity by sensing cardiac electrical signals to detect an abnormal rhythm. Pacemakers and ICDs may provide therapeutic electrical stimulation to the heart of the patient via electrodes carried by a medical electrical lead coupled to the pacemaker or ICD. The electrical stimulation may include pacing pulses to address abnormal cardiac rhythms such as bradycardia and ventricular tachycardia or cardioversion/defibrillation shocks for treating malignant forms of ventricular tachycardia and ventricular fibrillation. The reliability of an IMD in delivering electrical stimulation pulses and sensing electrical physiological signals for monitoring a patient depends at least in part on the integrity of the insulation and the electrical conductors of the medical electrical lead that carries electrodes used for delivering the therapeutic stimulation pulses and for sensing physiological signals.

SUMMARY

In general, the disclosure is directed to techniques for detecting medical electrical lead issues. An IMD as disclosed herein includes a spike detector for detecting non-physiological signal spikes. The IMD operates to identify non-physiological signal spikes that are likely to be caused by a lead issue and unlikely to arise from other non-physiological signal sources such as electromagnetic interference or therapeutic electrical stimulation pulses delivered by another medical device.

In one example, the disclosure provides an implantable cardiac device having a sensing module electrically coupled to one or more electrodes carried by a medical electrical lead coupled to the implantable medical device and a control module electrically coupled to the sensing module. The sensing module includes a cardiac event detector configured to receive a cardiac electrical signal sensed via at least one of the electrodes carried by the medical electrical lead coupled to the implantable medical device, detect cardiac event signals in the received cardiac electrical signal, and produce a cardiac sensed event signal for each of the detected cardiac event signals. The sensing module also includes a spike detector configured to receive the cardiac electrical signal, detect non-physiological spikes in the cardiac electrical signal, and produce a spike detect signal for each of the detected non-physiological spikes. The control module is configured to receive the cardiac sensed event signals and the spike detect signals from the sensing module and determine event intervals defined by consecutive ones of the received cardiac sensed event signals and the received spike detect signals. The control module is further configured to identify a received spike detect signal as a lead issue spike based on at least one of the determined event intervals, detect a lead issue of the medical electrical lead when a threshold number of spike detect signals are identified, and generate an alert in response to the lead issue being detected.

In another example, the disclosure provides a method of identifying a lead issue of a medical electrical lead. The method comprises receiving a cardiac electrical signal by a sensing module of an implantable medical device via electrodes carried by the medical electrical lead coupled to the implantable medical device, detecting cardiac event signals by a cardiac event detector of the sensing module, producing a cardiac sensed event signal for each of the detected cardiac event signals, detecting non-physiological spikes in the cardiac electrical signal by a spike detector of the sensing module, producing a spike detect signal for each of the detected non-physiological spikes, receiving the cardiac sensed event signals and the spike detect signals by a control module of the implantable medical device, determining event intervals defined by consecutive ones of the received cardiac sensed event signals and the received spike detect signals, identifying a received spike detect signal as a lead issue spike based on at least one of the determined event intervals, detecting a lead issue of the medical electrical lead when a threshold number of spike detect signals are identified, and generating an alert in response to detecting the lead issue.

In another example, the disclosure provides a non-transitory, computer readable storage medium comprising instructions which when executed by a control module of an implantable medical device cause the implantable medical device to determine event intervals defined by cardiac sensed event signals and spike detect signals produced by a cardiac event detector and a spike detector, respectively, of a sensing module of the implantable medical device, the sensing module configured to receive a cardiac electrical signal via electrodes carried by a medical electrical lead coupled to the implantable medical device. The instructions further cause the implantable medical device to identify a spike detect signal of the produced spike detect signals as a lead issue spike based on at least one of the determined event intervals, detect a lead issue of the medical electrical lead when a threshold number of spike detect signals are identified as lead issue spikes, and generate an alert in response to detecting the lead issue.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, an implantable medical device (IMD) is disclosed that is configured to sense cardiac electrical signals and deliver cardiac electrical stimulation therapies using electrodes coupled to the IMD via a medical electrical lead. The IMD is configured to detect lead issues, e.g., due to an insulation breach or an electrical conductor fracture of the lead, by detecting cardiac events and non-physiological electrical signal spikes on the cardiac electrical signal and determining and analyzing event intervals including at least one event interval beginning or ending with a detected signal spike.

Figure 1:
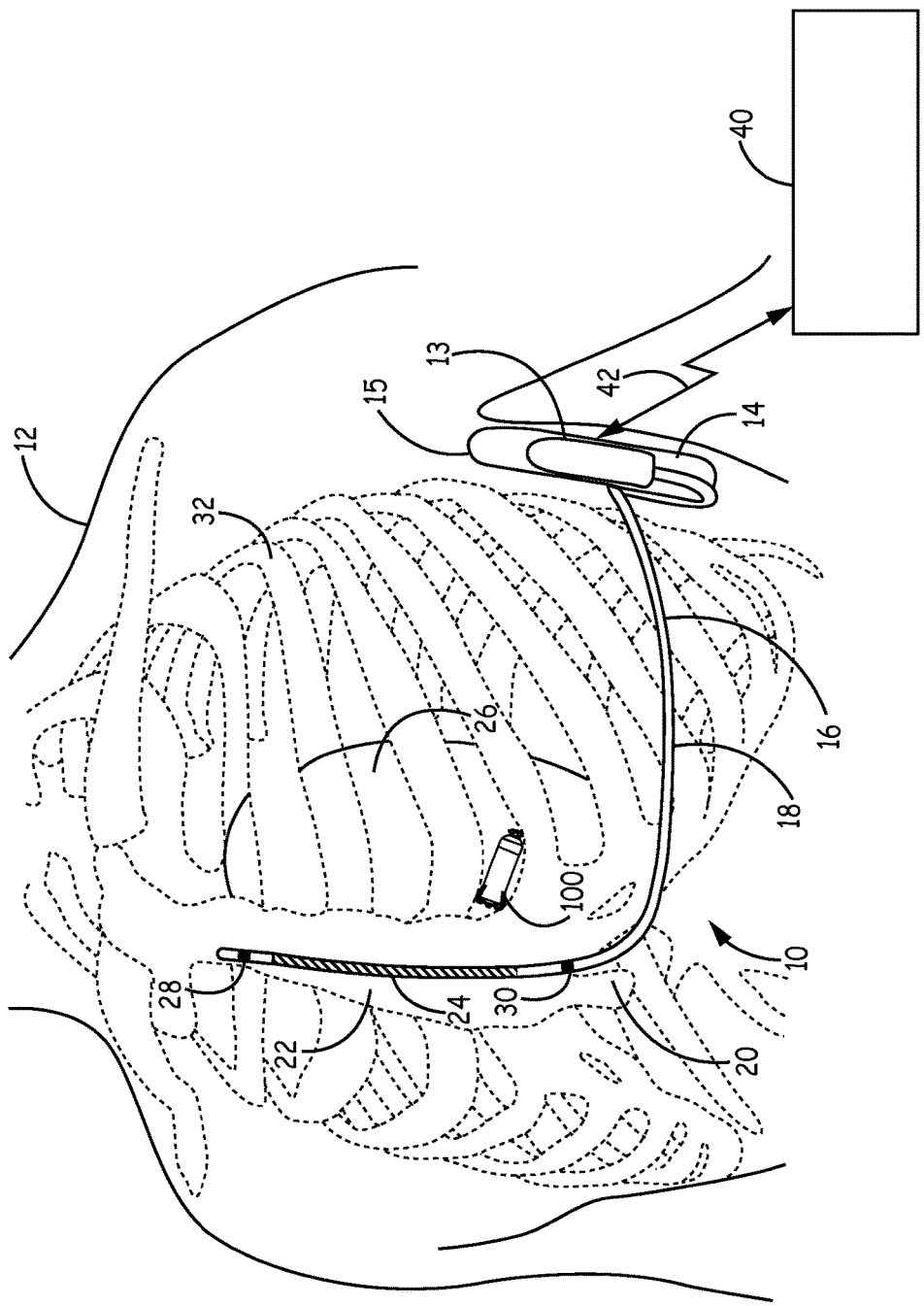
FIG. 1 is a conceptual diagram illustrating an IMD system used to sense cardiac electrical signals and provide therapy to a patient's heart.

FIG. 1 is a conceptual diagram illustrating an IMD system 10 used to sense cardiac electrical signals in patient 12 and provide therapy to heart 26. IMD system 10 includes an ICD 14 coupled to an extravascular medical electrical lead 16 for sensing cardiac electrical signals and/or delivering electrical stimulation therapies to heart 26 via electrodes carried by lead 16. ICD 14 is implanted subcutaneously on the left side of patient 12. Lead 16, which is connected to ICD 14, extends medially from ICD 14 toward sternum 22 and xiphoid process 20 of patient 12. At a location near xiphoid process 20, lead 16 bends or turns and extends subcutaneously superior, substantially parallel to sternum 22. Lead 16 may be implanted such that lead 16 is offset laterally to the left side of the body of sternum 22 (i.e., towards the left side of patient 12), offset to the right of sternum 22 or over sternum 22.

Lead 16 includes a defibrillation electrode 24, which may be an elongated coil electrode, and a pair of sensing electrodes 28 and 30. Lead 16 is placed along sternum 22 such that a therapy vector between defibrillation electrode 24 and the housing 15 of ICD 14 is substantially across one or both ventricles of heart 26. In other examples, another electrode along lead 16 or along a second lead coupled to ICD 14 may be used in combination with defibrillation electrode 24 for delivering a shock therapy.

In the example illustrated in FIG. 1, lead 16 is implanted subcutaneously, e.g., between the skin and the ribs or sternum. Lead 16 is advanced suprasternally remaining external to the thoracic cavity. In other embodiments, lead 16 may be advanced substernally or within ribcage 32, i.e., intra-thoracically. For example, lead 16 may be implanted at least partially in a substernal location. In such a configuration, a portion of lead 16 may extend subcutaneously from ICD 14 toward sternum 22 and at least a portion of lead 16 is advanced under or below the sternum in the mediastinum and, more particularly, in the anterior mediastinum. The anterior mediastinum is bounded laterally by pleurae, posteriorly by pericardium, and anteriorly by sternum 22. Lead 16 may be at least partially implanted in other intrathoracic locations, e.g., locations in and around heart 26, with or without making direct contact with the outer surface of heart 26, e.g., in epicardial or pericardial locations. In still other examples, lead 16 may be embodied as a transvenous, intracardiac lead that is advanced transvenously to position one or more electrodes within a patient's heart or its vasculature. An example of an ICD coupled to transvenous medical electrical leads is described below in conjunction with FIG. 4.

Although ICD 14 is illustrated in FIG. 1 as being implanted near a midaxillary line of patient 12, ICD 14 may also be implanted at other subcutaneous locations of patient 12, such as further posterior on the torso toward the posterior axillary line, further anterior on the torso toward the anterior axillary line, in a pectoral region, or at other locations of patient 12. In instances in which ICD 14 is implanted pectorally, lead 16 may follow a different path, e.g., across the upper chest area and inferior along sternum 22. When the ICD 14 is implanted in the pectoral region, lead 16 or a second lead including a defibrillation electrode may extend along the left side of the patient such that a defibrillation electrode is located along the left side of the patient to function as an anode or cathode of a therapy vector for defibrillating heart 26.

The techniques disclosed herein are not limited to a particular implant location of ICD 14 or medical electrical lead 16 coupled to ICD 14. Rather, the disclosed techniques for detecting a lead issue may be implemented in any IMD that is coupled to a medical electrical lead, configured to sense electrical signals, and is implanted at any desired anatomical location appropriate for a given medical application.

ICD 14 includes a housing 15 that forms a hermetic seal that protects electronic circuitry and other components within ICD 14. The housing 15 of ICD 14 may be formed of a conductive material, such as titanium or other biocompatible conductive material or a combination of conductive and non-conductive materials. In some instances, the housing 15 functions as an electrode (sometimes referred to as a housing electrode or "can" electrode) that is used in combination with one of electrodes 24, 28 and 30 to deliver a therapy to heart 26 or to sense electrical activity of heart 26.

ICD 14 includes a connector assembly 13 (sometimes referred to as a connector block or header) for receiving a proximal connector (not illustrated) of lead 16. Connector assembly 13 includes electrical feedthroughs through which electrical connections are made between electrical conductors within lead 16 and electronic components included within the housing.

Lead 16 includes an elongated lead body 18 having a proximal end that includes a connector configured to mate with connector assembly 13 of ICD 14 and a distal portion that includes electrodes 24, 28 and 30. The lead body 18 of lead 16 may be formed from a non-conductive, i.e., electrically insulating material, including silicone, polyurethane, fluoropolymers, mixtures thereof, or other appropriate materials, and is shaped to form one or more lumens within which the one or more electrical conductors (not illustrated) each extend to respective ones of electrodes 24, 28 and 30.

When the connector at the proximal end of lead 16 is connected to connector assembly 13, the respective electrical conductors electrically couple to circuitry of ICD 14, such as a therapy module and a sensing module via connections in connector assembly 13, including associated feedthroughs. The electrical conductors transmit electrical stimulation pulses from a therapy module within ICD 14 to one or more of electrodes 24, 28 and 30 and transmit sensed electrical signals from one or more of electrodes 24, 28 and 30 to the sensing module within ICD 14. Although lead 16 is illustrated as including three electrodes 24, 28 and 30, lead 16 may include more or fewer electrodes. For example, two or more sensing electrodes may be included for sensing a cardiac electrical signal, e.g. a subcutaneous electrocardiogram (ECG) signal.

ICD 14 may sense electrical activity of heart 26 from an ECG signal acquired via one or more sensing vectors that include combinations of electrodes 28 and 30 and housing 15. For example, ICD 14 may obtain ECG signals using a sensing vector between electrodes 28 and 30, between electrode 28 and housing 15, between electrode 30 and housing 15, or any combination thereof. In some instances, ICD 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15.

A lead performance issue may arise if the electrical insulation of a conductor extending to one of electrodes 24, 28 or 30 is breached or if one of the conductors extending through lead body 18 is fractured. An ECG received by ICD 14 may include electrical signal spikes caused by the lead issue, which are non-physiological in origin, as well as cardiac electrical signals that are physiological, i.e., electrophysiological signals attendant to the depolarization and repolarization of the myocardial tissue, such as R-waves, T-wave and P-waves. ICD 14 is configured to detect electrical signal spikes and determine if a detected electrical signal spike is likely due to a lead issue. Other non-physiological signal spikes may be present in the ECG signal due to other non-physiological signal sources, such as electromagnetic interference (EMI) or electrical stimulation pulses delivered by another medical device, such as pacemaker 100. ICD 14 is configured to detect non-physiological signal spikes, identify detected spikes that are likely due to a lead issue as opposed to arising from other signal sources, and detect a lead issue when a predetermined number or frequency of lead issue spikes are identified.

ICD 14 analyzes acquired ECG signals to detect ventricular tachyarrhythmias (VT), and in response to detecting VT may generate and deliver an electrical therapy to heart 26. For example, ICD 14 may deliver one or more defibrillation shocks via a therapy vector that includes defibrillation electrode 24 and the housing 15. In some instances, ICD 14 may be configured to deliver one or more pacing therapies, such as post shock pacing and/or ATP, which may depend in part on the lead and electrode system coupled to ICD 14.

Oversensing of noise spikes due to a lead issue could lead to a false detection of VT and/or impact therapy delivery. Accordingly, ICD 14 is configured to detect non-physiological spikes, determine if the spikes are likely due to a lead issue and generate an alert when a threshold number or frequency of lead issue spikes are detected. ICD 14 is capable of generating an alert that may be transmitted as a wireless telemetry communication signal to external device 40 to alert patient 12 or a clinician of the detected lead issue. In other examples, the alert may be an audible sound or mild electrical stimulation generated by ICD 14 and perceived by the patient.

In some instances, ICD 14 may be implanted in a patient having one or more other implanted medical devices configured to deliver electrical stimulation pulses to patient 12, such as a pacemaker or neurostimulator. In FIG. 1, an intracardiac pacemaker 100 is shown schematically as being implanted in a chamber of the patient's heart 26. Intracardiac pacemaker 100 may sense cardiac electrical signals and deliver therapeutic pacing pulses, such as bradycardia pacing or anti-tachycardia pacing (ATP), or other electrical stimulation pulses to heart 26.

An ECG signal sensed by ICD 14 via electrodes carried by lead 16 may include pacing spikes caused by pacing pulses delivered by pacemaker 100. In order to discriminate pacing spikes appearing on the ECG signal received by ICD 14 from true R-waves or other cardiac event signals that are physiological in origin and not originating from another device, ICD 14 includes a spike detector as described below in conjunction with FIG. 3. The spike detector detects high amplitude, high slew rate spikes to differentiate non-physiological pacing spikes caused by pacing pulses delivered by pacemaker 100 from physiological cardiac electrical signals in the ECG signal received by ICD 14. By detecting non-physiological signal spikes, false VT detection due to oversensing of pacing spikes is avoided. In addition to detecting signal spikes that are likely caused by pacing pulses delivered by pacemaker 100, ICD 14 is configured to determine if spikes detected by the spike detector are likely to be due to a lead issue of lead 16 rather than being pacing pulses delivered by pacemaker 100 (or another medical device delivering electrical stimulation pulses to patient 12).

In the example shown, pacemaker 100 is a transcatheter, intracardiac pacemaker adapted for implantation wholly within heart 26, e.g., wholly within the RV for delivering ventricular pacing therapies. ICD 14, however, may be implanted with a variety of other types of electrical stimulation devices, including, but not limited to, a pacemaker coupled to a transvenous lead, a pacemaker coupled to epicardial electrodes, a vagal nerve stimulator, a phrenic nerve stimulator, a spinal cord or other central or peripheral nerve stimulator, etc.

ICD 14 is capable of bidirectional wireless communication with an external device 40. External device 40 is often referred to as a "programmer" because it is typically used by a physician, technician, nurse, clinician or other qualified user for programming operating parameters in ICD 14. Operating parameters, such as sensing and therapy delivery control parameters, may be programmed into ICD 14 using external device 40. External device 40 may be located in a clinic, hospital or other medical facility. External device 40 may alternatively be embodied as a home monitor or a handheld device that may be used in a medical facility, in the patient's home, or another location. Aspects of external device 40 may generally correspond to the external programming/monitoring unit disclosed in U.S. Pat. No. 5,507,782 (Kieval, et al.), hereby incorporated herein by reference in its entirety.

External device 40 may be used to program operating parameters, such as sensing control parameters, tachyarrhythmia detection control parameters, and therapy delivery control parameters used by ICD 14. External device 40 may display programming data and information relating to ICD 14 functions to a user for reviewing ICD operation and programmed parameters as well as ECG signals or other physiological data that are retrieved from ICD 14 during an interrogation session.

External device 40 is configured for bidirectional communication with an implantable telemetry module included in ICD 14. External device 40 establishes a wireless radio frequency (RF) communication link 42 with ICD 14 for sending and receiving data via communication link 42. Communication link 42 may be established between ICD 14 and external device 40 via a radio frequency (RF) link in the Medical Implant Communication Service (MICS) band, Medical Data Service (MEDS) band, BLUETOOTH® wireless communication standard, Wi-Fi or other RF bandwidth.

External device 40 may be capable of bi-directional communication with ICD 14 over a wide range of distances, e.g., up to approximately 10 meters. In other examples, telemetry communication with ICD 14 may require the use of a programming head placed in proximity of ICD 14 to facilitate data transfer. It is contemplated that external device 40 may be in wired or wireless connection to a communications network for transferring data to a remote database or computer to allow remote management of ICD 14.

Figure 2:
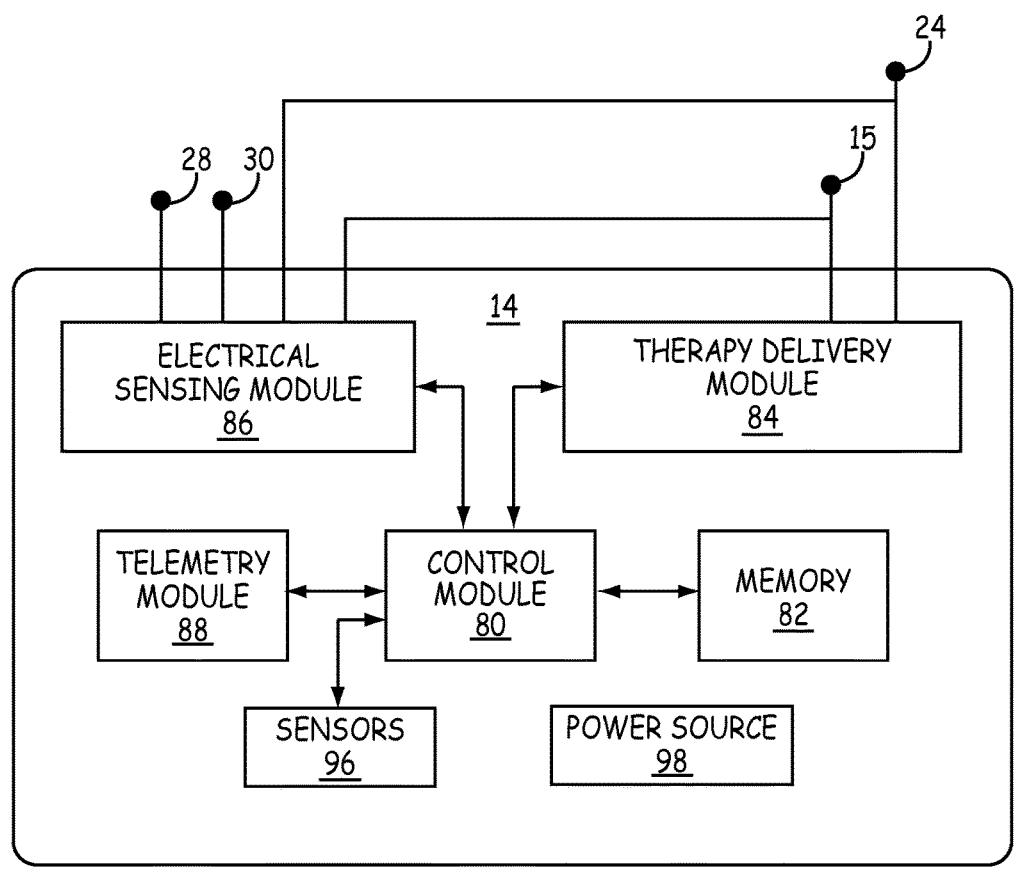
FIG. 2 is a schematic diagram of the ICD included in the system of FIG. 1 according to one example.

FIG. 2 is a schematic diagram of ICD 14 according to one example. The electronic circuitry enclosed within housing 15 includes software, firmware and hardware that cooperatively monitor one or more ECG signals, determine when a CV/DF shock is necessary, and deliver prescribed CV/DF therapies. ICD 14 is coupled to a lead, such as lead 16 shown in FIG. 1, carrying electrodes, such as electrodes 24, 28 and 30, positioned in operative relation to the patient's heart for sensing cardiac electrical signals and delivering therapeutic electrical stimulation, e.g., CV/DF shocks and post-shock pacing during recovery.

ICD 14 includes control module 80, memory 82, therapy delivery module 84, electrical sensing module 86, and telemetry module 88. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 2 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, application specific integrated circuits (ASICs), memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal.

The functional operation of ICD 14 as disclosed herein should not be construed as reflective of a specific form of software or hardware necessary to practice the methods described. It is believed that the particular form of software, hardware and/or firmware will be determined primarily by the particular system architecture employed in ICD 14. Providing software, hardware, and/or firmware to accomplish the described functionality in the context of any modern IMD, given the disclosure herein, is within the abilities of one of skill in the art.

Control module 80 communicates with therapy delivery module 84 and electrical sensing module 86 for sensing cardiac electrical activity, detecting cardiac rhythms, and generating electrical stimulation therapies in response to sensed signals. Therapy delivery module 84 is electrically coupled to defibrillation electrode 24 and housing 15 for delivering electrical stimulation therapies such as CV/DF shocks. In some examples, therapy delivery module 84 may additionally be coupled to electrodes 28 and 30 for use in delivering therapy and/or delivering mild electrical stimulation for generating a patient alert.

Electrical sensing module 86 is electrically coupled to electrodes 24, 28, and 30 carried by lead 16 (shown in FIG. 1) and housing 15, which may serve as a common or ground electrode. Electrical sensing module 86 is selectively coupled to sensing electrodes 28, 30 and housing 15 in order to monitor electrical activity of the patient's heart. Electrical sensing module 86 may additionally be selectively coupled to defibrillation electrode 24. Sensing module 86 may be enabled to monitor one or more sensing vectors selected from the available electrodes 24, 28, 30 and 15. For example, sensing module 86 may include switching circuitry for selecting which of electrodes 24, 28, 30 and housing 15 are coupled to sense amplifiers or other cardiac event detectors included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors selected from electrodes 24, 28, 30 and housing 15. For example, sensing module 86 may include two sensing channels. Each sensing channel may include a sense amplifier or other cardiac event detection circuitry for sensing cardiac events, e.g., R-waves, from the received ECG signal developed across the selected electrodes 24, 28, 30 or 15. The cardiac event detector may operate using an auto-adjusting sensing threshold set based on a peak amplitude of a currently sensed event that may decay over time. Each time the received ECG signal crosses the auto-adjusting sensing threshold outside an absolute blanking period, a cardiac sensed event signal, such as an R-wave sensed event signal, is produced and passed to control module 80 for use in detecting VT.

Control module 80 is configured to detect VT episodes that may be life-threatening if left untreated, generally referred to herein as a "shockable rhythm," such as non-sinus ventricular tachycardia or ventricular fibrillation. The timing of R-wave sensed event signals received from sensing module 86 may be used by control module 80 to determine RR intervals between cardiac sensed event signals. Control module 80 may count RR intervals that fall into different rate detection zones for determining a ventricular rate or performing other rate- or interval-based assessments for detecting VT and discriminating VT from rhythms that do not require a CV/DF shock.

Sensing module 86 may include an analog-to-digital converter for providing a digital ECG signal from one or all available sensing channels to control module 80 for further signal analysis for use in VT detection. A sensed ECG signal may be converted to a multi-bit digital signal by sensing module 86 and provided to control module 80 for performing ECG morphology analysis. Analysis of the ECG signal morphology may be performed for detecting, confirming or discriminating VT.

Examples of algorithms that may be performed by ICD 14 for detecting, discriminating and treating shockable rhythms are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety. The detection algorithms are highly sensitive and specific for the presence or absence of life threatening, shockable VT. Methods disclosed herein for detecting a lead issue may be implemented in any of the IMDs described as being coupled to a medical electrical lead in the incorporated references.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by control module 80 to apply or withhold a therapy.

Therapy delivery module 84 includes a high voltage (HV) therapy delivery module including one or more HV output capacitors and, in some instances, a low voltage therapy delivery module. When a shockable VT rhythm is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using defibrillation electrode 24 and housing 15.

Each sensing channel included in electrical sensing module 86 includes spike detector circuitry for detecting non-physiological electrical signal spikes present in the cardiac electrical(s) received by sensing module 86. Non-physiological signal spikes may be caused by electrical stimulation pulses delivered by another implanted device, such as pacemaker 100. The spike detector produces a spike detect signal passed to control module 80 for use in detecting a lead issue as well as avoiding false detections of VT due to oversensing of electrical spikes that are not true R-waves. In some examples, sensing module 86 is configured to detect pacing pulses delivered to heart 26 by pacemaker 100. For example, when both ICD 14 and pacemaker 100 are implanted in a patient, bradycardia pacing pulses or anti-tachycardia pacing pulses delivered by pacemaker 100 may be detected by the spike detector of sensing module 86. The spike detector may be implemented according to the apparatus and techniques for detecting pacing pulses as generally disclosed in U.S. patent application Ser. No. 14/687,053 (Reinke, et al.), filed on Apr. 15, 2015, incorporated herein by reference in its entirety.

Control module 80 may receive spike detection output signals from the spike detector (from one or more sensing channels) to prevent pacing spikes from being counted as R-waves in tachyarrhythmia detection algorithms. Control module 80 is configured to analyze the timing of spike detect signals received form sensing module 86 as described below to identify non-physiological spikes that are unlikely to be a pacing spike or EMI and are therefore likely to be lead issue spikes. Spikes that are unlikely to be caused by a pacing pulse or EMI are identified as lead issue spikes and can lead to detection of a lead issue by control module 80.

Control module 80 is configured to determine event intervals between cardiac sensed event signals and spike detect signals received from sensing module 86. Any combination of two consecutive signals received from sensing module 86 may define an event interval, e.g., R-sensed event signals and spike detect signals, and one or more event intervals are compared to lead issue spike detection criteria for identifying spikes that are more likely caused by a lead issue than other non-physiological signal sources. Event intervals determined by control module 80 may include R-S intervals, S-R intervals, S-S intervals and R-R intervals for example. An R-S interval is determined as the interval from an R-sensed event signal to a spike detect signal that consecutively follows the R-sensed event signal without any intervening R-sensed event signal. An S-R interval is determined as the interval from a spike detect signal to an R-sensed event signal that consecutively follows the spike detect signal. An S-S interval is determined when two consecutive spike detect signals occur with no intervening R-sensed event signal, and an R-R interval is determined between two consecutive R-sensed event signals occur with no intervening spike detect signal. These various R-S, S-R, S-S, and R-R event intervals are used by control module 80 for discriminating spike detect signals likely to be due to a lead issue from spike detect signals likely to be due to electrical stimulation pulses delivered by another device or EMI, as further described below.

Control module 80 may be configured to generate a patient or physician alert in response to lead issue detection criteria being met. For example, an alert may be generated upon a predetermined number or frequency of spike detect signals being identified as lead issue spikes. The alert may be a communication signal transmitted by telemetry module 88, mild electrical stimulation delivered by therapy delivery module 84 via any of electrodes 24, 28, 30 or 15, an audible alert generated by an acoustic transducer included in sensors 96 or other alert signal perceptible by the patient or transmitted and received by an external device such as device 40 of FIG. 1.

User-programmable sensing and therapy delivery control parameters may be programmed into memory 82 via telemetry module 88. Telemetry module 88 includes a transceiver and antenna for communicating with external device 40 (shown in FIG. 1) using RF communication or other communication protocol. Telemetry module 88 may receive downlink telemetry from and send uplink telemetry to external device 40.

ECG episode data related to detected spikes that are identified as lead issue spikes may be stored in memory 82 and transmitted by telemetry module 88 to external device 40 upon receipt of an interrogation command. Clinician or technician review of ECG episodes that include spike detection data facilitates proper diagnosis of a lead issue, enabling corrective action to be taken, such as reprogramming ICD 14 to use different therapy and/or sensing vectors or replacement of lead 16.

Figure 3:
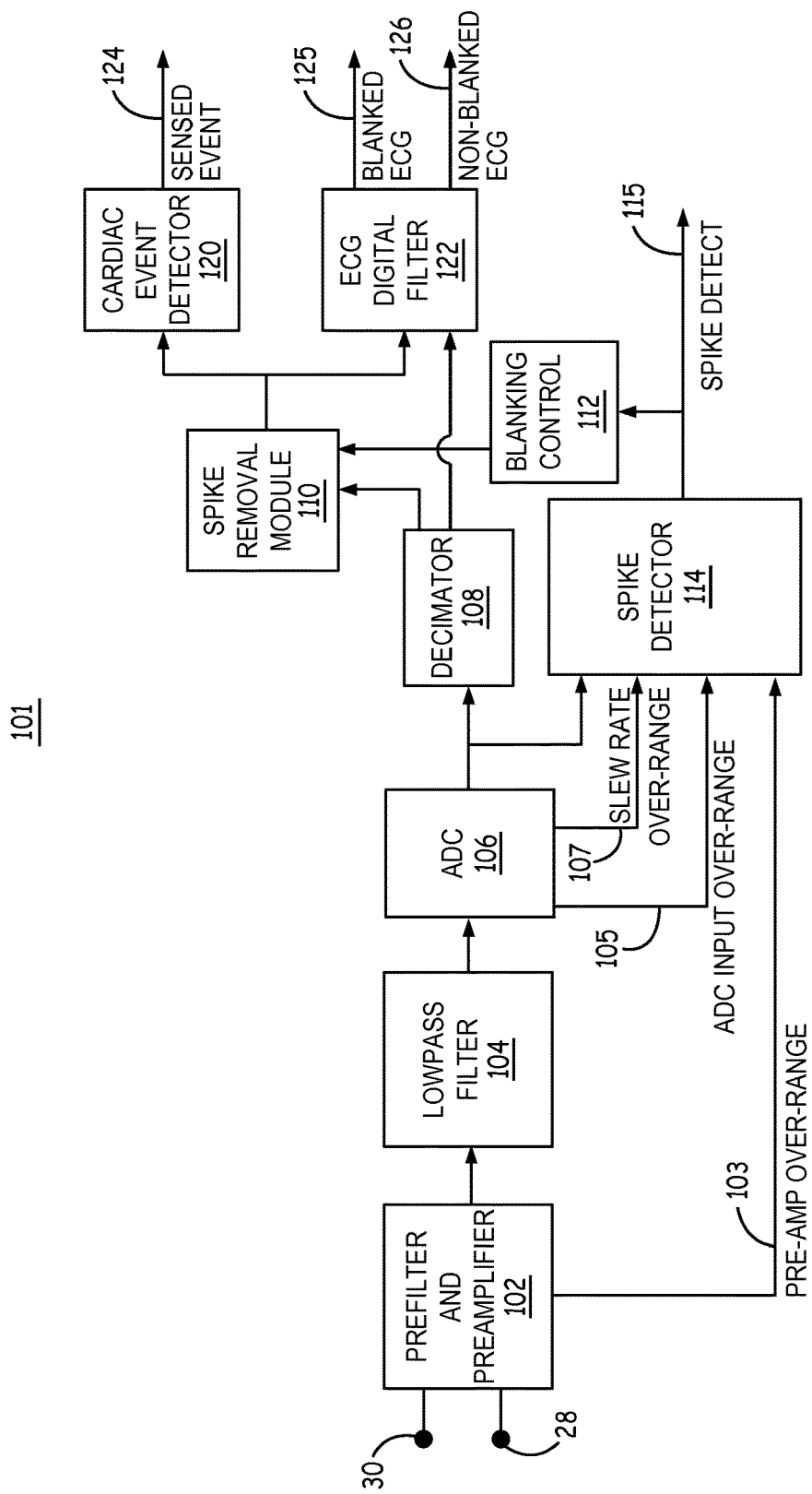
FIG. 3 is a block diagram of an example sensing channel included in a sensing module of FIG. 2.

FIG. 3 is a block diagram of an example sensing channel 101 of sensing module 86 of FIG. 2. The sensing channel 101 may receive an electrical signal developed across input electrodes, e.g., electrodes 28 and 30, coupled to sensing channel 101. Sensing channel 101 is shown coupled to electrodes 28 and 30 in this example, but other electrodes or other combinations of available electrodes may be coupled to sensing channel 101. Sensing module 86 may include multiple sensing channels similar to sensing channel 101 for each sensing vector signal to be analyzed for use in detecting VT and for detecting signal spikes. In the case of multiple sensing channels, sensing module 86 may include duplicate components for each sensing channel 101, or the sensing channels may share one or more components.

In this example, sensing channel 101 includes a pre-filter and pre-amplifier 102, low-pass filter 104, analog-to-digital converter (ADC) 106, decimator 108, spike removal module 110, spike blanking control 112, spike detector 114, cardiac event detector 120 and ECG digital filter 122. The configuration of sensing channel 101 is illustrative in nature and should not be considered limiting of the techniques described herein. The sensing channel 101 of sensing module 86 may include more or fewer components than illustrated and described in FIG. 3. Sensing channel 101, however, does include a hardware-based spike detector 114 for detecting non-physiological signal spikes in some examples. Software or firmware based algorithms for detecting suspected non-physiological signal spikes from the cardiac electrical signal need not be performed by control module 80. In other words, the spike detector 114 may be a hardware implemented spike detector that provides control module 80 with a spike detect signal when a non-physiological signal spike occurs without control module 80 having to perform algorithmic analysis of the morphology of the cardiac electrical signal for detecting the non-physiological signal spike. Once the spike detect signal is received, control module 80 performs a time-interval based analysis of spike detect signals and cardiac sensed event signals to discriminate lead issue spikes from other non-physiological signal sources.

The electrical signal developed across input electrodes 28 and 30 is provided as a differential input signal to pre-filter and pre-amplifier 102. Non-physiological high frequency and DC signals may be filtered by a bandpass filter included in pre-filter and pre-amplifier 102, and high voltage signals may be removed by protection diodes included in pre-filter and pre-amplifier 102. Pre-filter and pre-amplifier 102 amplifies the pre-filtered signal by a gain of between 10 and 50, and in one example a gain of 17.5, and may convert the differential signal to a single-ended output signal passed to low pass filter 104.

Pre-filter and pre-amplifier 102 may, in some examples, generate a pre-amp over-range signal 103 when the pre-filtered signal exceeds a range of the pre-amplifier input. For example, an amplifier included in pre-filter and pre-amplifier 102 may have an input range of approximately ±10 to 20 millivolts (mV); however, the input range may be smaller or larger in other examples. Pre-filter and pre-amplifier 102 may generate the pre-amp over-range signal 103 when the input signal causes the preamplifier to be over-range. Such a condition may be evidence of a non-physiological input signal that is greater than approximately 10 to 20 mV input range, larger than the expected amplitude of a physiological cardiac electrical signal, e.g., an R-wave corresponding to a ventricular contraction, which might typically be in the range of 1 to 5 mV. The pre-amp over-range signal 103 may be provided to spike detector 62 for use in detecting non-physiological signal spikes.

The pre-amplified signal output of pre-filter and pre-amplifier 102 is passed to low pass filter 104. Low pass filter 104 may provide anti-alias filtering and noise reduction prior to digitization. The filtered signal output of low pass filter 104 is passed to ADC 106, which converts the analog signal to a digital bit stream. In one example, ADC 106 may be a sigma-delta converter (SDC), but other types of ADCs may be used. The output of ADC 106 may be provided to decimator 108, which functions as a digital low-pass filter that increases the resolution and reduces the sampling rate. In one example, ADC 106 may have an 8-bit resolution and 16 or 32 kiloHertz (kHz) sampling rate. Decimator 108 may have a 16-bit resolution and a 1 kHz sampling rate. These values are intended for illustrative purposes only and should not be considered limiting of the techniques described herein.

ADC 106 may have other characteristics, such as an input range and a slew rate range. In one example, the input amplitude range of ADC 106 may be between 25 and 825 mV. ADC 106 may be configured to generate an ADC input over-range signal 105 when the input signal amplitude is greater than the input amplitude range of ADC 106. For example if the preamplifier had a gain of 17.5 and an input signal change of 25 mV, the output of the preamplifier would change from approximately 425 mV to approximately 850 mV causing the ADC input to exceed the maximum input range. Such a condition may, for example, be indicative of a non-physiological signal spike that is larger than an expected R-wave or other physiological event of the ECG.

Alternatively or additionally, ADC 106 may be configured to generate a slew rate over-range signal 107 when the slew rate is faster than can be tracked by ADC 106. For example, the accumulated voltage error signal internal to ADC 106 may be monitored with a comparator and when the error signal exceeds the comparator threshold, the slew over-range signal 107 is generated. In one example, the slew-rate over-range signal 107 may be generated when the slew rate of the ADC input signal is greater than or equal to 54 mV/ms corresponding to a signal at the input of the preamplifier of approximately 3 mV/ms. The ADC input over-range signal 105 and/or the slew rate over-range signal 107 are provided to spike detector 114 for detecting non-physiological signal spikes.

The digitized signal output from decimator 108 may be provided to the cardiac event detector 120 and the ECG digital filter 122. Cardiac event detector 120 may include a bandpass filter (e.g., 10 to 32 Hz), rectifier, and threshold crossing detector. The cardiac event detector 120 may, in one example, operate by setting an auto-adjusting sensing threshold that dynamically varies from a percentage of the peak value of the currently detected cardiac event signal, e.g., the peak amplitude of a sensed R-wave, and a programmed minimum value according to one or more decay rates or step drops. A sensed event signal 124 is output from cardiac event detector 120 and passed to control module 80 to indicate that a cardiac event is detected, e.g., an R-wave, when the received electrical signal exceeds the cardiac event sensing threshold.

Cardiac event detector 120 may apply a post-sense blanking period after a sensing threshold crossing. A post-sense blanking period prevents the same cardiac signal from being sensed twice by cardiac event detector 120. A post-sense blanking period may be applied by setting the sensing threshold to a maximum value such that a threshold crossing cannot be detected. During the blanking period the peak signal amplitude of the currently sensed event is determined, e.g., by a peak tracking circuit. Upon expiration of the blanking period, the sensing threshold is adjusted to a percentage of the peak amplitude of the sensed event. During the post-sense blanking period, which is typically 120 ms, or in the range of 80 ms to 140 ms, cardiac event detector 120 is effectively disabled from producing a sensed event signal 124.

In some examples, control module 80 is configured to perform signal morphology analysis of the cardiac electrical signal. In this case, ECG digital filter 122 may apply a bandpass filter (e.g., with a bandwidth of 2.5 to 32 Hz) to provide a filtered, digitized ECG signal to control module 80 for performing morphology analysis according to implemented VT detection algorithms.

Spike detector 114 receives the output of ADC 106 for detecting non-physiological signal spikes. For example, spike detector 114 may be configured to detect non-physiological signal characteristics of a pacing spike caused by a pacing pulse delivered by another therapy delivery device implanted in the patient. For example, spike detector 114 may use comparators or other hardware-based techniques for detecting an amplitude of the signal received from ADC 106, slew rate, or other feature that is characteristic of a pacing pulse signal that is not physiological in origin. Spike detector 114 may include a filter configured to pass electrical signals corresponding to pacing pulses and reject intrinsic or evoked cardiac electrical event signals such as R-waves, P-waves or T-waves (e.g., a filter that passes signals having frequencies greater than 100 Hz). Alternatively or additionally, spike detector 114 may include a differentiator, difference filter, or a first order derivative filter that may be used to obtain a signal representative of the slew rate of the sensed signal.

Spike detector 114 may also include one or more threshold detectors. In another example, spike detector 114 may include a slew rate threshold detector that compares the output of a differentiator or a first order derivative filter to a slew rate threshold. If the slew rate exceeds the slew rate threshold, spike detector 114 determines that the signal has characteristics of a pacing pulse (or other non-physiological signal spike). Spike detector 114 may additionally or alternatively analyze the amplitude of the input signal received from ADC 106 for detecting a signal having signal characteristics of a pacing spike. For example, if the slew rate exceeds a slew rate threshold and the amplitude exceeds an amplitude threshold, a spike detection may be made.

In some cases, a high slew rate, high amplitude signal having characteristics that are non-physiological is caused by EMI or a lead issue. As such the slew rate and amplitude criteria used to detect a signal spike by spike detector 114 may not be specific to detecting spikes caused by therapeutic electrical stimulation pulses delivered by another medical device. Detected spikes may arise from other non-physiological signal sources such as EMI or lead issues.

In addition to receiving the ADC output signal, spike detector 114 may receive the pre-amp over-range signal 103 from pre-filter and pre-amplifier 102, the ADC input over-range signal 105 from ADC 106, and the slew rate over-range signal 107 from ADC 106. All or at least some of these signals may be indicative of a signal spike. For example, a preamplifier over-range signal 103 or an ADC input over-range signal 105 may be indicative of a signal spike that is much larger than an expected ventricular depolarization signal, i.e., an R-wave. As another example, ADC slew rate over-range signal 107 may be indicative of a signal spike since an R-wave would not exceed a slew rate limit of the ADC 106. As such, each of these over-range signals indicate the presence of a signal spike, which may be caused by a pacing pulse delivered by pacemaker 100, a lead issue, or EMI. Spike detector 114 may receive these over-range signals 103, 105 and 107 for use in detecting signal spikes in response thereto in addition to amplitude and/or slew rate thresholds applied to the ADC output signal. In some instances, however, spike detector 114 may detect signal spikes using only the sensed electrical signal output by ADC 106.

If spike detection criteria are met, spike detector 114 generates a spike detect signal 115 that is passed to control module 80. In some examples, the spike detect signal 115 is passed to a blanking control 112 that initiates a spike blanking period applied by spike removal module 110. During the spike blanking period, spike removal module 110 adjusts the signal output from decimator 108 to remove or substantially diminish the spike from the electrical signal passed to cardiac event detector 120.

Spike removal module 110 may, in one example, include a sample and hold circuit that holds the value of the electrical signal at a current value in response to receiving a control signal from spike blanking control 112. The current value may be a value of the electrical signal from decimator 108 prior to the spike detect signal. In another example, spike removal module 110 may interpolate a signal value determined from one or more signal values before and/or after the spike detect signal 115 is produced. Spike removal module 110 holds the value of the electrical signal for the spike blanking period, which may be until the blanking control 112 removes the control signal.

During the spike blanking period, the detected spike is removed from the cardiac electrical signal passed to cardiac event detector 120. Cardiac event detector 120 may remain enabled to detect cardiac sensing threshold crossings and produce sensed event signals 124, but since the spike is removed or "blanked" from the incoming signal, a sensing threshold crossing during the spike blanking period is highly unlikely. In other examples, the cardiac event detector 120 may be disabled from sensing a cardiac event during the spike blanking period.

The spike blanking period may be approximately 20 ms to 40 ms, but may be longer or shorter than these intervals in other examples. In some cases, the spike blanking period is selected to be long enough to effectively remove a pacing spike from the signal received by cardiac event detector 120. In this way, when ICD 14 is implanted with another therapy delivery device such as pacemaker 100, pacing pulses delivered by pacemaker 100 that cause a pacing spike on the cardiac electrical signal received by sensing channel 101 are substantially removed and go undetected by cardiac event detector 120. The spike blanking period is kept as short as possible to remove the pacing spike without "blinding" cardiac event detector 120 any longer than necessary and enable high rate true cardiac events to be detected and appropriately result in sensed event signals 124.

Spike removal module 110 or another component of sensing channel 101 may, in some instances, include a delay block that introduces a delay into the electrical signal prior to the sample and hold circuit to allow for detection of a spike by spike detector 114 and processing time required to remove the signal spike before it is passed to cardiac event detector 120. The delay introduced into the sensing channel 101 may be between approximately 1 to 20 ms. In some instances, this introduced delay is not required since decimator 108 may provide some inherent delay between the ADC output and the spike removal module 110.

By removing the spike from the output of decimator 108 for a spike detection blanking period, cardiac event detector 120 does not falsely detect spikes in the electrical signal as intrinsic R-waves, thus reducing the likelihood of oversensing pacing pulses delivered by pacemaker 100. In some examples, the output of spike removal module 110 is provided as the input to ECG digital filter 122. A "blanked" ECG signal 125 may be output by ECG digital filter 122 to provide control module 80 with a cardiac electrical signal with detected spikes removed or substantially eliminated from the signal. In this way, pacing spikes caused by pacing pulses delivered by pacemaker 100 do not confound the ECG morphology analysis that may be performed by control module 80 for VT detection.

In other examples, the output from decimator 108 is provided to ECG digital filter, additionally or instead of the output from spike removal module 110. ECG digital filter 122 provides a non-blanked ECG signal 126 to control module 80 that includes spikes detected by spike detector 114. Control module 80 may be configured to perform morphology analysis of detected spikes in the non-blanked ECG signal 126 in order to identify lead issue spikes.

Control module 80 may perform analysis of detected spikes for discriminating between lead issue spikes and spikes caused by other sources such as EMI or therapy pulses delivered by another implanted therapy delivery device such as pacemaker 100. At certain times, the non-blanked ECG signal 126 may be stored by memory 82 under the control of control module 80 so that ECG signal episodes that include spikes detected by spike detector 114 and identified as lead issue spikes by control module 80 are available for review by a clinician or technician.

Control module 80 is further provided with spike detect signals 115 from spike detector 114 for detecting a lead issue. If the frequency of spike detect signals reaches a predetermined frequency threshold for detecting a lead issue, ICD 14 may generate an alert. For example, with no limitation intended, if 30 spike detect signals are received over a three day period, a lead issue alert may be generated. A greater number of spikes or a smaller number of spikes may be required over a shorter or longer period of time in order to cause a lead issue alert to be generated. Lead issue detection criteria may include a threshold number of lead issue spikes being identified and may require that the threshold number of lead issue spikes be reached within a predefined time interval.

A lead issue spike may have a wider signal width (longer duration) than a pacing spike. As such, in some cases a detected spike caused by a lead issue may still be present after the spike blanking period has expired. This situation could lead to a cardiac event sensing threshold crossing and a sensed event signal produced by cardiac event detector 120 immediately after the spike blanking period expires. Since lead issues are expected to be rare, the spike blanking period may be kept to the shortest duration possible to "blank" pacing spikes from the signal received by cardiac event detector 120 since such spike can be frequent when pacemaker 100 or another therapy delivery device is present in the patient. A cardiac sensed event signal 124 closely coupled in time to a spike detect signal 115, e.g., within a very short interval of the spike blanking period expiration, may be evidence of a lead issue spike. These and other criteria for identifying lead issue spikes are further described below.

The sensing channel 101 illustrated in FIG. 3 is one example of a sensing channel that may be implemented in conjunction with the techniques disclosed herein. Other configurations of a sensing channel or arrangement of components in the sensing channel may be utilized. In other examples, spike detector 114 may obtain its input from other components earlier in the sensing channel processing stage or spike removal module 110 may be located elsewhere within the sensing channel, such as between prefilter and preamplifier 102 and low-pass filter 104.

Figure 4:
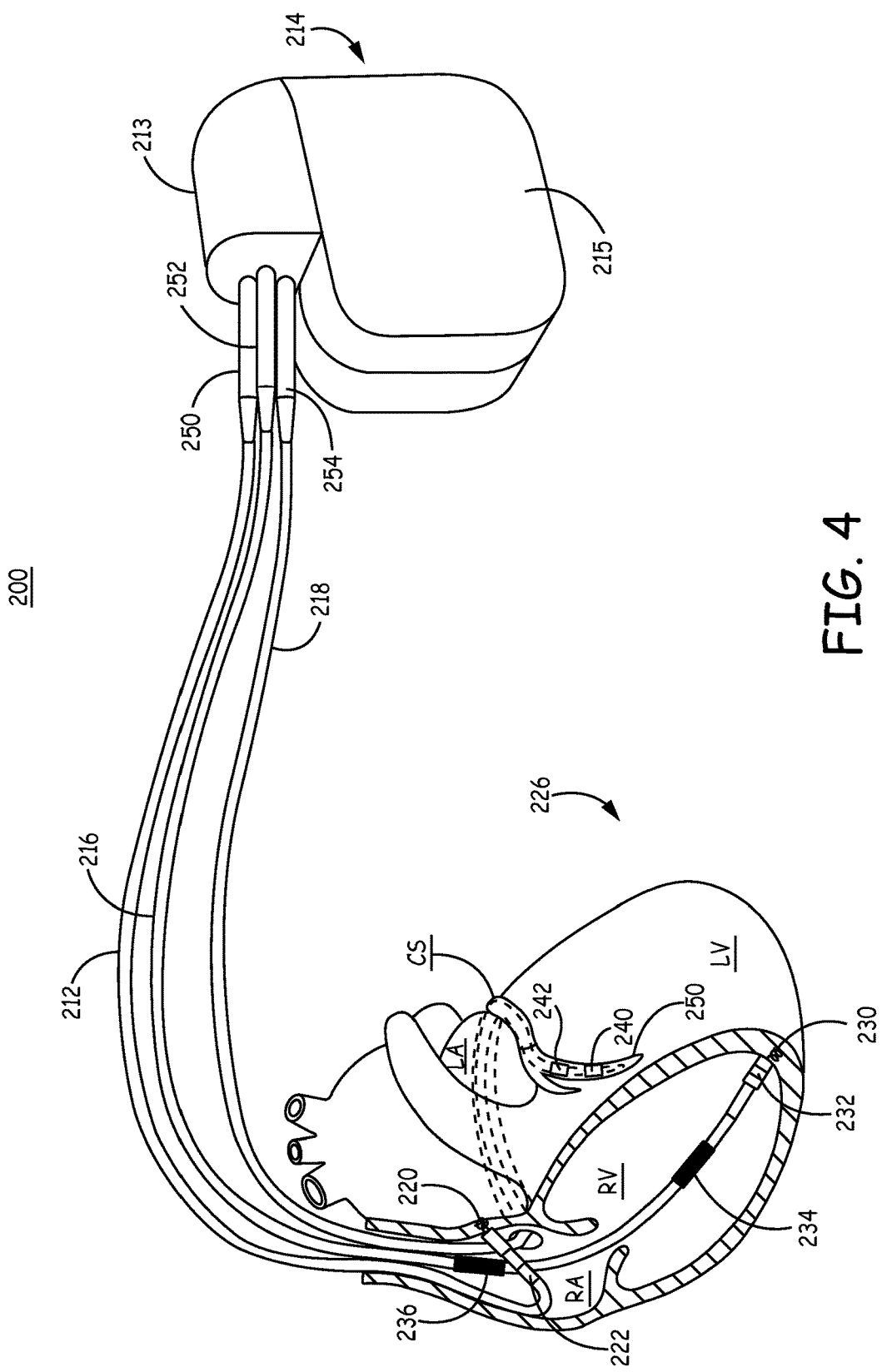
FIG. 4 is a schematic representation of an IMD system according to another example.

FIG. 4 is a schematic representation of an IMD system 200 that includes an ICD 214 capable of delivering high voltage and low voltage therapies to heart 226. Sensing channel 101 of FIG. 3 including a spike detector is described above in the context of ICD 14 shown in FIG. 1 coupled to an, extracardiac, extravascular lead 16. However, the presently disclosed techniques for detecting and discriminating lead issue spikes and generating a lead issue alert may be implemented in other IMD systems that include transvenous lead(s) that may extend into heart 226, such as IMD system 200.

ICD 214 is coupled to heart 226 via leads 212, 216, and 218. Right atrial lead 212 extends from ICD 214 to the right atrium (RA) and carries distal electrodes 220 and 222 for sensing cardiac electrical signals and delivering pacing pulses in the RA. In addition, IMD housing 215 may be used as a return electrode in combination with electrodes 220 and/or 222 to deliver the pacing pulses in the RA.

Right ventricular lead 216 carries a tip electrode 230 and a ring electrode 232 for sensing cardiac electrical signals and delivering pacing pulses in the RV. RV lead 216 may additionally carry high voltage electrodes 234 and 236, referred to herein as the RV defibrillation electrode 234 and the superior vena cava (SVC) defibrillation electrode 236, for delivering high voltage cardioversion and defibrillation shocks in response to detecting a shockable VT from sensed cardiac signals. Housing 215 may be used with pace/sense electrodes 230 and 232 for delivering RV pacing pulses or in combination with defibrillation electrodes 234 and/or 236 during shock delivery.

A coronary sinus (CS) lead 218 is shown extending into a cardiac vein 250 via the RA and coronary sinus for positioning electrodes 240 and 242 for sensing cardiac signals and delivering pacing pulses along the left ventricle (LV). In some examples, CS lead 18 may additionally carry electrodes for positioning along the left atrium (LA) for sensing and stimulation along the left atrial chamber. CS lead 218 may carry additional electrodes positioned along the left ventricle, e.g., four electrodes or more for providing multiple selectable pacing or sensing vectors. Housing 215 may be used as an electrode in combination with electrodes 240 and/or 242 to deliver the pacing pulses to the LV.

The depicted positions of leads 212, 216 and 218 in or about the right and left heart chambers are merely illustrative. Other leads and pace/sense electrodes and/or high voltage CV/DF electrodes can be used instead of, or in combination with, any one or more of the depicted leads and electrodes shown in FIG. 3. ICD 214 is shown as a multi-chamber device capable of sensing and stimulation in three or all four heart chambers. It is understood that ICD 214 may be modified to operate as a single chamber device, e.g. with a lead positioned in the RV only, or a dual chamber device, e.g. with a lead positioned in the RA and a lead positioned in the RV.

In general, ICD 214 may be embodied as any single, dual or multi-chamber device configured to receive at least one medical electrical lead by a connector assembly 213 having one or more bores for mating with a respective number of lead connectors. One or more electrodes carried by a lead coupled to ICD 214 is used for sensing cardiac electrical signals and may be used for delivering therapy to heart 226. ICD 214 may be embodied as an ICD capable of delivering both low voltage pacing pulses and high voltage CV/DF shocks or as a pacing device only for delivering low voltage pacing therapies.

Each of leads 212, 216 and 218 include insulated electrical conductors extending from the respective electrodes 220, 222, 23, 232, 234, 236, 240 and 242 to a respective proximal connector 250, 252, or 254 that electrically couples the electrodes to circuitry enclosed by housing 215 when the proximal connectors 250, 252 and 254 are properly positioned in IMD connector assembly 213. Circuitry enclosed in housing 215 may generally correspond to the modules and their associated functions shown and described in conjunction with FIG. 2 above. The techniques disclosed herein for detecting lead issues may be applied to any of the leads 212, 216 and 218.

As such, ICD 214 includes a sensing module 86, which may include multiple sensing channels, one, some or all of which may be represented by sensing channel 101 shown in FIG. 3 including spike detector 114. In this case, sensing channel 101 may receive an intracardiac electrogram (EGM) signal from electrodes positioned within a heart chamber rather than the ECG signal acquired via extracardiac electrodes as described in conjunction with ICD 14 of FIG. 1. Either of these cardiac electrical signals, i.e., an ECG or EGM, acquired using electrodes carried by a medical electrical lead coupled to the associated ICD 14 or ICD 214 may include spikes caused by a lead issue enabling detection of the lead issue by the control module 80 of the respective ICD 14 or ICD 214 according to the techniques disclosed herein.

Figure 5:
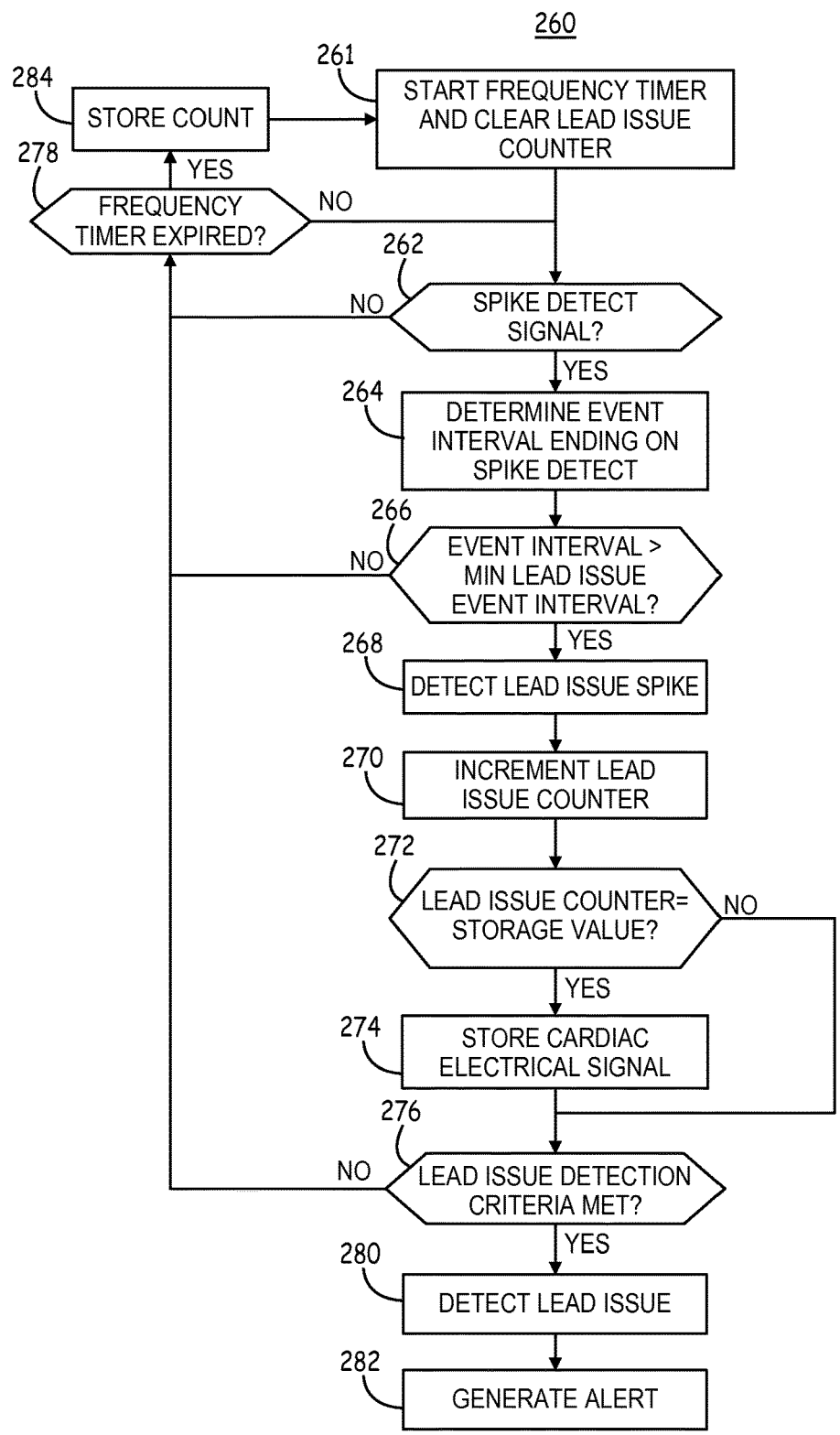
FIG. 5 is a flow chart of one method for detecting a lead issue based on spike detect signals according to one example.

FIG. 5 is a flow chart 260 of one method for detecting a lead issue based on spike detect signals received from sensing channel 101 according to one example. The process shown by flow chart 260 may be implemented in the ICD 214 shown in FIG. 4 or in the ICD 14 shown in FIG. 1 and may be used when no other therapy delivery device is present in (or on) the patient. When no other therapy delivery device is present, spikes that are detected by spike detector 114 will most likely be caused by EMI or a lead issue but are not due to a pacing or other electrical stimulation pulse delivered by another medical device. As such, a lead issue spike can be identified by discriminating lead issue spikes from spikes that are likely caused by EMI.

At block 261, a frequency timer and a lead issue spike counter included in control module 80 are initialized for tracking the number and frequency of spike detect signals received from spike detector 114 that are identified as lead issue spikes. A lead issue may be detected by control module 80 when a required number of lead issue spikes are identified or when a required number of lead issue spikes are identified within a predetermined period of time, i.e., a required frequency of lead issue spikes is met. The frequency timer may be set to one or more minutes, one or more hours, one or more days, e.g., on hour, one day, three days, or other selected time interval, at block 261.

Control module 80 waits for a spike detect signal from spike detector 114 at block 262. If the frequency timer expires at block 278 while waiting for a spike detect signal at block 262. The lead issue spike detection count for the current frequency time interval may be stored in memory at block 284 in some examples to allow a combination of multiple lead issue counts obtained over multiple respective frequency time intervals to be compared to lead issue detection criteria. The frequency timer and lead issue counter are re-initialized at block 261.

If a spike detect output signal is received by control module 80 at block 262, control module 80 determines the event time interval between the most recent preceding event signal received from sensing channel 101 and the currently received spike detect signal at block 264. The most recent preceding event signal may be a cardiac sensed event signal, such as a P-wave sensed event signal or an R-wave sensed event signal, received from cardiac event detector 120 or a preceding spike detect signal received from spike detector 114. As such, the event interval determined at block 264 may be an interval between a preceding cardiac sensed event signal received from cardiac event detector 120 to the currently received spike detect signal or an interval between two consecutively received spike detect signals. To illustrate, if the sensing channel 101 providing the spike detect signal received at block 262 is a ventricular sensing channel, the time interval ending on the currently received spike detect signal may be an R-S interval or an S-S interval.

The time interval ending on the currently received spike detect signal is compared to criteria for identifying the spike detect signal as a lead issue spike and not an EMI spike at block 266. In one example, the criteria for identifying a lead issue spike include the requirement that the event interval ending on a spike detect signal be greater than a minimum lead issue event interval since the most recently preceding event signal. As such, the event interval determined at block 264 is compared to a minimum lead issue event interval at block 266. In one example, the minimum lead issue event interval is an applied blanking period plus a predefined EMI exclusion time interval (e.g., N ms).

The blanking period may be a post-sense blanking period applied by cardiac event detector 120 or a spike blanking period applied by blanking control 112 and spike removal module 110. The post-sense blanking period is applied by cardiac event detector 120 after a sensed event signal is generated and precludes double sensing of the same cardiac event by cardiac event detector 120. The post sense blanking period may be approximately 100 to 150 ms but may be more or less than this range depending on the particular IMD or ICD and sensing channel. In one example, the post sense blanking period is 120 ms. The minimum lead issue event interval for detecting a lead issue spike is set at the blanking period plus an EMI exclusion interval, e.g., 20 ms. Thus, in one example, the minimum lead issue event interval is 140 ms.

If the most recent preceding event is a spike detect signal, the applied blanking period is the spike blanking period. In this case the blanking period may be 20 ms and the EMI exclusion interval may be 20 ms to provide a minimum lead issue event interval applied at block 266 of 40 ms. The blanking period used corresponds to the type of event that preceded the currently received spike detect signal, and the EMI exclusion interval is selected to exclude spike detect signals received within an EMI cycle time after the end of the applied blanking period from being identified as lead issue spikes.

To illustrate, if EMI is present on the cardiac electrical signal, multiple EMI spikes may be removed or blanked from the cardiac electrical signal during a blanking period applied by spike removal module 110 or by cardiac event detector 120. If EMI is present, the first EMI spike outside an applied blanking period may occur less than 20 ms after the end of that blanking period (if 60 Hz noise is present, EMI spikes may occur approximately every 8 ms in the rectified cardiac electrical signal) or less than 40 ms after the blanking period (if 16 Hz noise is present causing EMI spikes every 33 ms in the rectified cardiac signal). If the first spike detect signal received after the applied blanking period is within the EMI exclusion interval, e.g., up to 40 ms after the blanking period, at block 266, the spike detect signal may be an EMI spike and is therefore not identified as a lead issue spike. Control module 80 returns to block 262 to wait for the next spike detect signal as long as the frequency timer has not expired, as determined at block 278 before returning to block 262.

If the event interval determined at block 264 is longer than the currently applied blanking interval plus the EMI exclusion interval (block 266), the spike detect signal received from detector 114 is identified as a lead issue spike at block 268 by control module 80. The lead issue counter initialized to zero at block 261 is incremented by one at block 270. If the lead issue counter has reached a storage value, as determined at block 272, an episode of the cardiac electrical signal may be stored at block 274. The stored signal may be the non-blanked ECG (or EGM) signal output received from decimator 108 and filtered by ECG (or EGM) digital filter 122 that includes the spike signal. The stored signal may alternatively be the blanked ECG (or EGM) signal received by digital filter 122 from spike removal module 110. In some examples, both the blanked cardiac electrical signal (processed by spike removal module 110) and the non-blanked cardiac electrical signal (not processed by spike removal module 110) are stored. In other examples, the cardiac electrical signal output from another component of sensing channel 101 may be stored at block 274, such as the output of prefilter and preamplifier 102, output of lowpass filter 104 or output of decimator 108, which provides the cardiac electrical signal without blanking of the detected spike by spike removal module 110. The cardiac electrical signal may be stored each time the lead issue counter reaches predefined storage values, e.g., when the lead issue counter reaches a value of 1, 10, 20, and 30 or any other predefined values.

At block 276, the detected lead issue count(s) for one or more frequency time intervals are compared to lead issue detection criteria. In one example, the lead issue count for a single frequency time interval, e.g., one hour or one day, is compared to a lead issue detection threshold. In another example, the counts for multiple frequency time intervals may be individually compared to a lead issue detection threshold and/or summed and compared to a combined count lead issue detection threshold. In one example, 30 lead issue spikes are required within three days in order to detect a lead issue. The lead issue count obtained over three consecutive 24-hour frequency time intervals may be summed and compared to the 3-day threshold or a single 3-day count may be compared to the 3-day threshold. In another example, 10 lead issue spikes within one hour or within 24 hours may cause lead issue detection. In still other examples, a frequency criterion is not used and whenever a threshold number of lead issue spikes are identified, e.g., 50 lead issue spikes, a lead issue is detected.

The frequency timer and lead issue counter initialized at block 261 provide one technique for control module 80 to determine whether lead issue detection criteria are met, but it is recognized that other techniques for tracking the number and frequency of detected lead issue spikes may be implemented. In the example shown, the lead issue detection criteria can become satisfied during the frequency time interval if a current count of detected lead issue spikes, or a current count summed with preceding frequency time interval counts, reaches a detection threshold. In other examples, the lead issue detection criteria may be applied only after a frequency time internal expires and uses the total count(s) obtained over one or more expired frequency time intervals.

If the lead issue detection criteria are not met at block 276, and the frequency timer has not expired, as determined at decision block 278, the control module 80 waits for the next spike detect signal at block 262. If the frequency timer expires (block 278), control module 80 resets the frequency timer and the lead issue counter at block 261 to begin counting lead issue spikes during the next frequency time interval.

If the lead issue detection criteria are satisfied at block 276, control module 80 detects a lead issue at block 280 and generates an alert at block 282. In this way, spikes detected by the spike detector 114 of sensing channel 101 are used to detect a lead issue as well as prevent cardiac event oversensing and false VT detection.

Figure 6:
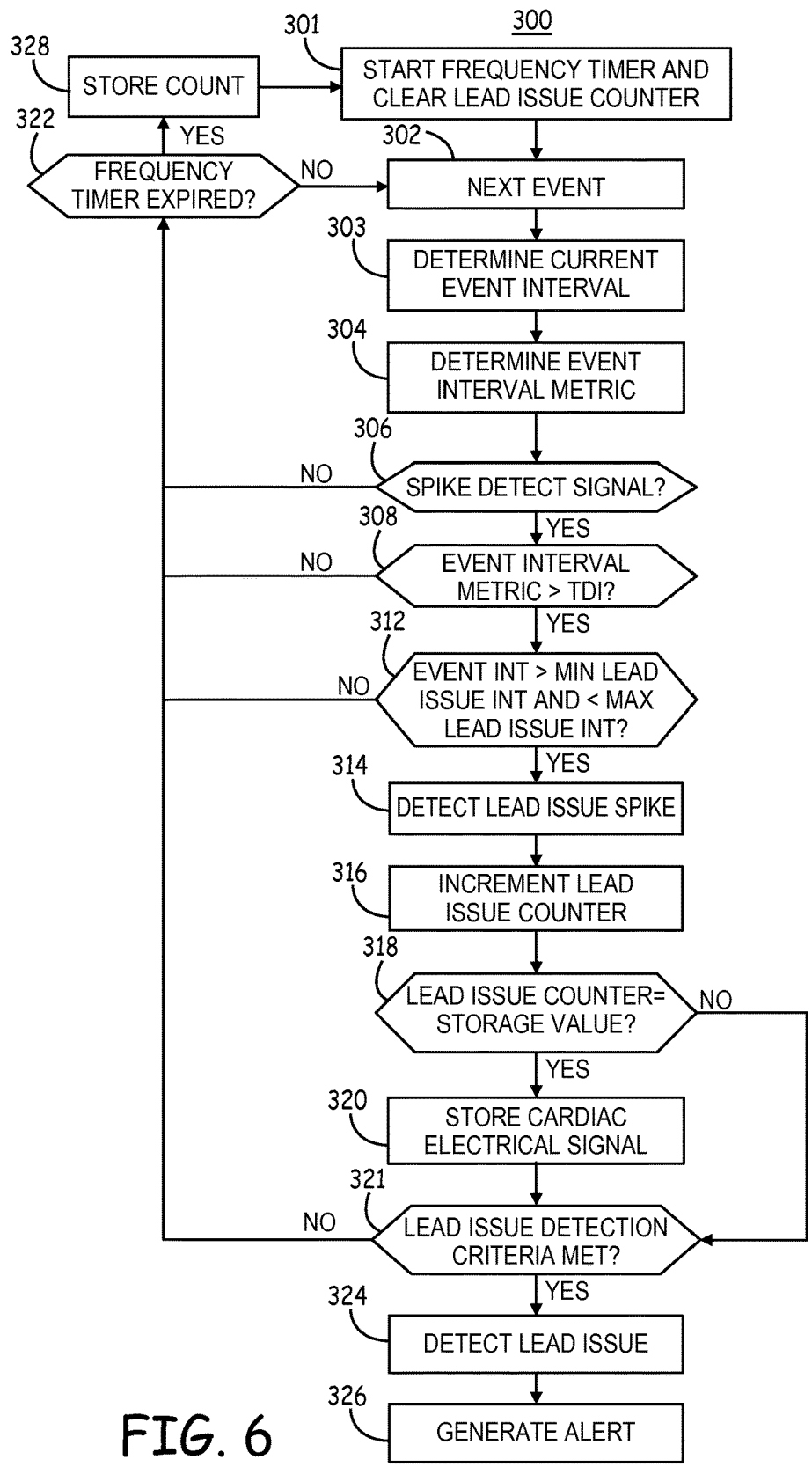
FIG. 6 is a flow chart of a method for identifying a lead issue according to another example.

FIG. 6 is a flow chart 300 of a method for identifying a lead issue according to another example. The process of flow chart 300 for detecting a lead issue is implemented in an IMD when another therapy delivery device is present in the patient. Flow chart 300 is described in the context of ICD 14 when pacemaker 100 is present as shown in FIG. 1. The process of flow chart 300, however, may be implemented in other pacemakers, ICDs or cardiac signal monitors when another therapy delivery device is present in or on the patient. ICD 14 may be programmed manually to enable the lead issue detection process shown by flow chart 300 when pacemaker 100 is co-implanted.

Alternatively, ICD 14 may be configured to automatically detect the presence of pacemaker 100 based on receipt of a communication signal from pacemaker 100 or by detecting pacing pulses delivered by pacemaker 100. Detection of pacing pulses may be performed as generally disclosed in U.S. patent application Ser. No. 14/686,947 (Reinke, et al.), incorporated herein by reference in its entirety. ICD 14 may switch between the process shown by flow chart 260 of FIG. 5 and the process shown by flow chart 300 of FIG. 6 as needed based on the absence or presence of another therapy delivery device, respectively. Switching between the two processes may be automatic when a second device is recognized automatically by ICD 14 or in response to manual programming by a clinician.

At block 301, control module 80 starts a frequency timer and initializes a lead issue counter to zero as described above with respect to flow chart 260 of FIG. 5. ICD 14 receives a cardiac electrical signal by sensing channel 101 via at least one electrode carried by lead 16, and control module 80 receives event signals from sensing channel 101 at block 302. The event signals may be cardiac sensed event signals 124, spike detect signals 115 or both. Upon receiving an event signal from sensing channel 101 at block 302, control module 80 computes a current event interval at block 303.

At block 304, control module 80 determines an event interval metric from a predetermined number of preceding event intervals. The preceding event intervals may include intervals between two cardiac sensed event signals from cardiac event detector 120, two spike detect signals from spike detector 114, or one cardiac sensed event signal and one spike detect signal (with the spike detect signal ending the interval or starting the interval). The event interval metric may be a maximum, median, predetermined percentile (e.g., $75^{th}$ percentile) or other statistical event interval metric determined from the immediately preceding predetermined number of consecutive event intervals. The consecutive event intervals may be any combination of R-R, R-S, S-R, or S-S intervals as they occur. The current event interval ending with the current event signal received at block 302 is not used in updating the event interval metric at block 304. Rather, the current event interval is compared to the updated event interval metric determined from preceding event intervals as described below.

In one example, the maximum event interval out of three consecutive event intervals preceding the current event interval is determined. In other examples, the maximum event interval of more than three preceding event intervals, e.g., five to eight event intervals, is determined. The maximum event interval is stored and updated upon each event signal received by control module 80 as the maximum event interval out of the predetermined number of preceding event intervals.

If the current event signal received from sensing module 101 at block 302 is a cardiac event signal, the process returns to block 322 to check if the frequency timer has expired. If not, control module 80 waits for the next event signal (spike detect signal or cardiac event signal) at block 302. The current event interval determined at block 303 will be used to update the event interval metric at block 304 after the next event signal is received at block 302.

If the current event signal received from sensing channel 101 is a spike detect signal, the currently stored event interval metric is compared a tachyarrhythmia detection interval (TDI) at block 308. The TDI may be 500 ms or another value considered to discriminate event intervals that are not evidence of tachyarrhythmia. The TDI may be set equal to a TDI used by pacemaker 100 for detecting tachyarrhythmia when TDI of pacemaker 100 is known. Otherwise a nominal or programmable TDI is used for the comparison at block 308 in ICD control module 80.

If the currently stored event interval metric is less than the TDI, pacemaker 100 may be detecting tachyarrhythmia and delivering ATP. A spike detect signal received by control module 80 of ICD 14 when the event interval metric is less than the TDI is not identified as a lead issue spike since there is a possibility that the spike is a pacing spike due to an ATP pulse delivered by pacemaker 100.

A true lead issue spike may go unidentified in this case if pacemaker 100 is not pacing. Undersensing of lead issue spikes when there is an increased likelihood of ATP delivery by pacemaker 100, however, may be acceptable. Over the course of the frequency timer, it is expected that if a true lead issue exists, a threshold number of lead issue spikes will be positively identified at times that there is a decreased likelihood of ATP delivery by the pacemaker 100 (i.e., when the event interval metric is greater than the TDI at block 308) so that an appropriate lead issue detection can still be made. By not identifying spike detect signals as being lead issue spikes when the event interval metric is less than a TDI, a false detection of a lead issue is avoided.

Additionally or alternatively, ICD 14 may utilize other techniques at block 308 for determining that the spike detect signal is likely due to ATP or other trains or bursts of stimulation pulses being delivered by another implanted device. Techniques that may be used by ICD 14 for detecting ATP or other trains of stimulation pulses are generally disclosed in the above-incorporated U.S. patent application Ser. No. 14/686,947 (Reinke, et al.). Spike detect signals that are determined to be ATP or other stimulation pulse trains are not counted by the lead issue spike detection counter.

If the event interval metric is greater than the TDI (block 308) when the spike detect signal is received (and/or is not identified as being part of a train of stimulation pulses according to the techniques of the above incorporated '947 application), the current event interval ending with the spike detect signal is compared to lead issue spike detection criteria at block 312. In the example of FIG. 6, the lead issue spike detection criteria require that the current event interval is greater than a minimum lead issue event interval and less than a maximum lead issue event interval. As described above in conjunction with FIG. 5, the minimum lead issue event interval may be an applied blanking period (upon the preceding cardiac sensed event signal or spike detect signal, whichever occurred most recently) plus an EMI exclusion interval (N ms) to eliminate spikes in the cardiac electrical signal that may be caused by EMI.

When another therapy delivery device is present in the patient, the control module 80 may additionally compare the event interval ending with the spike detect signal to a maximum lead issue event interval at block 312. The maximum lead issue event interval is defined to avoid identifying pacing spikes as lead issue spikes. A pacing pulse interval (that is not an ATP interval) is not expected to be significantly shorter than the event interval metric currently stored. If pacing is occurring at a steady rate, the pacing pulse interval is expected to be approximately equal to the event interval metric. If the pacing rate is decreasing, and the spike ending the current event interval is caused by a pacing pulse, the current event interval will be longer than the currently stored event interval metric. If the pacing rate is increasing, e.g., based on a patient activity signal for providing rate responsive pacing, the pacing pulse interval is expected to decrease, possibly shorter than the event interval metric, but only by a limited decrement since abrupt changes in pacing rate are generally avoided.

Accordingly, a spike detection interval that is approaching or greater than the event interval metric has a high likelihood of being a pacing spike. The maximum lead issue event interval may be set based on the currently stored event interval metric to discriminate between lead issue spikes and spikes that are more highly likely to be pacing spikes. The maximum lead issue event interval may, in one example, be set to the event interval metric less a pacing exclusion interval (X ms). In one example, the pacing exclusion interval is 40 to 100 ms but other intervals greater than or less than this range may be selected based on the expected pacing behavior of pacemaker 100. The pacing exclusion interval may be set to be at least a maximum expected one-step decrement used to adjust a pacing interval by pacemaker 100.

To illustrate, if pacemaker 100 is a rate responsive pacemaker, the rate response function may cause the pacing interval to be decreased by a maximum decrement of 40 ms from one paced beat to the next. In another example, pacemaker 100 is configured to perform tests, such as a pacing capture test that requires shortening a pacing interval below an intrinsic heart rate interval. Pacemaker 100 may set a test pacing interval to be no more than 40 ms less than the currently sensed intrinsic heart rate intervals. As these examples illustrate, knowing the expected pacing behavior of pacemaker 100 when decreasing a pacing interval, the maximum lead issue event interval can be set based on a predetermined number of preceding event intervals and an expected maximum pacing interval decrement.

If pacemaker 100 is pacing at a regular pacing rate, pacing pulses delivered by pacemaker 100 may be detected as spikes by ICD 14. Event intervals that are S-S intervals will occur at the regular pacing rate. As such, an event interval ending with a spike detect signal, e.g., an S-S interval, will not be less than the event interval metric determined as the maximum event interval (in this case an S-S interval occurring at the regular pacing rate) less the pacing exclusion interval since the pacing rate is not expected to suddenly decrease by more than the pacing exclusion interval. The pacing exclusion interval criterion avoids identifying spike detect signals as lead issue spikes when pacemaker 100 is pacing the heart at a regular rate.

If pacemaker 100 is a rate responsive pacemaker that shortens the pacing pulse interval to increase pacing rate to meet a metabolic need of the patient, the pacemaker 100 may gradually shorten the pacing interval such that the S-S event intervals gradually shorten. The pacing exclusion interval, X ms, however is selected to be larger than the amount the pacing interval would be shortened from one beat to the next or within the predetermined number of event intervals used to determine the event interval metric. The pacing exclusion interval is set to exclude spike detect signals that are likely to be pacing pulses delivered by pacemaker 100 at a gradually increasing rate for rate responsive pacing.

The requirement of the maximum lead issue event interval reduces the likelihood of control module 80 identifying a pacing spike as a lead issue spike. A spike detect signal ending an event interval that is greater than the minimum lead issue event interval and less than the maximum lead issue event interval is identified as a lead issue spike at block 314. In one example, a spike detect signal ending an event interval that is greater than an applied blanking period plus the EMI exclusion interval and less than the event interval metric less the pacing exclusion interval is detected as a lead issue spike.

If the comparisons of the event interval to the minimum lead issue interval and the maximum lead issue interval at block 312 are not satisfied, the spike detect signal is not detected as a lead issue spike. The process returns to block 322. If the frequency timer expires at block 322, e.g., while control module 80 is waiting for a spike detect signal at block 306, after determining that the event interval metric is greater than the TDI at block 308, or after determining that the event interval does not meet the lead issue spike detection criteria at block 312, the current lead issue count may be stored for the currently expired frequency time interval at block 328. The count value is stored when it is used on combination with one or more other lead issue counts obtained during other frequency time intervals. The frequency timer and lead issue counter are re-initialized at block 301. If the frequency timer has not expired at block 322, the process returns to block 302 to wait for the next event signal.

When a lead issue spike is detected at block 314 while the frequency timer is running, the lead issue counter is incremented by one at block 316. As described above in conjunction with FIG. 5, if the lead issue counter reaches a storage value, the blanked and/or non-blanked cardiac electrical signal may be stored at block 320. At block 321, lead issue detection criteria are applied to the lead issue count, which may be compared directly to a lead issue detection threshold and/or summed with one or more prior frequency time interval counts as described above in conjunction with FIG. 5. If the lead issue detection criteria are satisfied, control module 80 detects a lead issue at block 324 and generates an alert at block 326.

Figure 7:
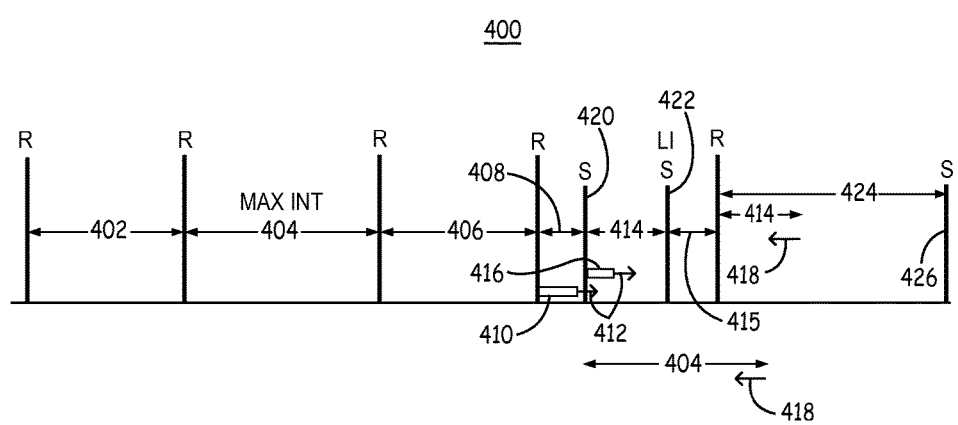
FIG. 7 is a conceptual diagram of event signals and associated time intervals determined by and used for time interval-based discrimination of lead issue spikes.

While the illustrative implementation of lead issue detection criteria is described herein as using a frequency timer and counter, it is recognized that other techniques may be used for arriving at a lead issue detection based on a required number and/or frequency of lead issue spike detections within one or more defined time intervals. When time intervals are included in the lead issue detection criteria, the time intervals may be relatively short time intervals (e.g., one or more cardiac cycles or one or more minutes), relatively long time intervals (e.g., one or more hours, days or weeks), and may include a required number of lead issue spikes during a most recent time interval and/or historic time intervals. FIG. 7 is a conceptual diagram 400 of event signals produced by sensing channel 101 and associated time intervals determined by control module 80 and used for time interval-based discrimination of lead issue spikes according to the method described above in conjunction with FIG. 6. A sequence of R-wave sensed event signals are received by control module 80 at consecutive event intervals 402, 404 and 406. In this example, the event interval metric determined at block 304 of FIG. 6 is the maximum event interval out of three preceding event intervals, e.g., intervals 402, 404, and 406 (excluding the current event interval 408 ending on the current event signal 420). Event interval 404 is determined as the maximum event interval, i.e., the event interval metric in this example, of these three consecutive intervals 402, 404, 406.

The next event interval 408 ending in a spike detect signal 420 is compared to the post-sense blanking period 410 applied by cardiac event detector 120 plus the EMI exclusion interval 412. Since spike detect signal 420 occurs within this minimum lead issue event interval set to the blanking period 410 plus the EMI exclusion interval 412, spike detect signal 420 is not identified as a lead issue spike because it is within an EMI cycle length of the end of blanking period 410.

The next event interval 414 ends in a spike detect signal 422. The maximum event interval of the three preceding event intervals 404, 406 and 408 is still interval 404. Control module 80 compares event interval 414 to the minimum lead issue event interval that is now set to the spike blanking period 416 applied by spike removal module 110 plus the EMI exclusion interval 412. Control module 80 also compares the event interval 414 to the maximum lead issue event interval that is set to the maximum event interval 404 less the pacing exclusion interval 418. Since the spike detect signal 422 occurs later than the blanking period 416 plus the EMI exclusion interval and earlier than the currently stored maximum event interval 404 less the pacing exclusion interval 418, spike detect signal 422 is identified as a lead issue spike (LIS). The lead issue counter is incremented in response to spike detect signal 422.

Event intervals 402, 404, 406, and 415 that end on R-sense event signals are used in updating the event interval metric but since these R-sense event signals are not spike detect signals, criteria for identifying lead-issue spikes are not applied to event intervals 402, 404, 406 and 415. The next event interval 424 that ends in a spike detect signal 426 is longer than maximum lead issue event interval set to the updated maximum event interval 414 (maximum of the preceding event intervals 408, 414, and 415) less the pacing exclusion interval 418. Spike detect signal 426 may be a pacing pulse delivered by pacemaker 100 and is not identified as a lead issue spike.

Figure 8A:
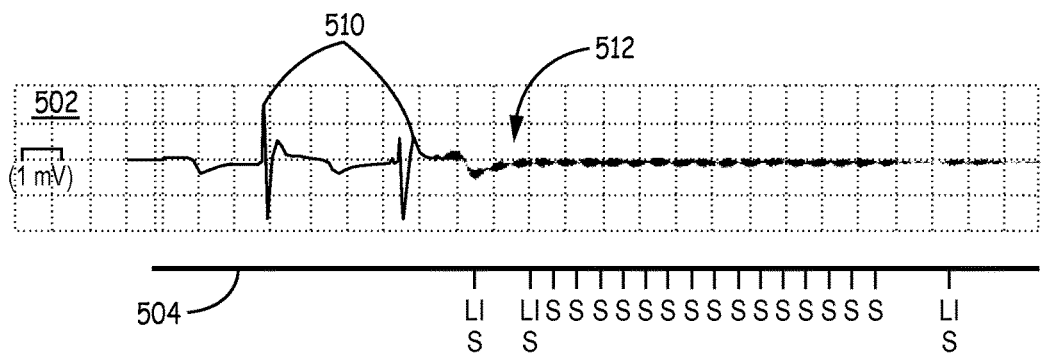
FIGS. 8A and 8B show an example recording of a cardiac electrical signal and a spike detection marker channel including spikes detected during an episode of electromagnetic interference.

FIG. 8A is a recording of a cardiac electrical signal 502 and a spike detection marker channel 504. The cardiac electrical signal 502 is received by an IMD via electrodes carried by a lead coupled to the IMD. The IMD may correspond to ICD 214 in FIG. 4 in which case the ICD 214 delivers the pacing pulses 510. The sensing channel 101 is blanked during pacing pulse delivery so that the pacing pulses 510 are not detected by spike detector 114. No other therapy delivery device is present in the patient in this example. ICD 214 may therefore be configured to perform the method described above in conjunction with FIG. 5 for detecting a lead issue.

The two pacing pulses 510 are followed by an episode of EMI 512. The spike detector 114 of ICD 214 produces a series of spike detect signals, which are denoted on the spike detection marker channel 504 by S (spike) and LIS (lead issue spike) based on whether the detected spike is identified as a lead issue spike. In this example, the spike blanking period expires and a spike detect signal immediately follows. Spike removal module 110 removes the detected spike signal from the signal passed to cardiac event detector 120 so no cardiac sense event signal is produced. Upon expiration of the spike blanking period, another spike is immediately detected within the cycle length of the EMI after the blanking period expires, resulting in another spike blanking period. A post-sense blanking period applied by the cardiac event detector 120 may be set to 120 ms such that upon expiration of each post-sense blanking period the EMI causes an immediate cardiac sensed event signal just outside the blanking period.

In the example of the ICD 214 delivering the pacing pulses 510 with no other therapy delivery device present in the patient, the control module 80 of ICD 214 identifies each spike detect signal (S) as a lead issue spike (LIS) when the event interval ending with the spike detect signal is greater than the minimum lead issue event interval as described in conjunction with the flow chart of FIG. 5. In this example, the minimum lead issue event interval may be the applied blanking period, which is the spike blanking period in this case, plus an EMI exclusion interval. Spike detection markers labeled "S" occur at an event interval that is less than an applied blanking period plus the EMI exclusion interval and are not identified as lead issue spikes. The signal spikes labeled "S" on spike detection marker channel 504 are not counted for detecting a lead issue but the detection of the EMI spikes prevents false sensing of cardiac events due to EMI 512 and an improper detection of VT. As described in conjunction with FIG. 3, blanking control 112 may control spike removal module 110 to blank the spikes detected during EMI 512 so that the EMI 512 is not sensed by cardiac event detector 120.

Figure 8B:
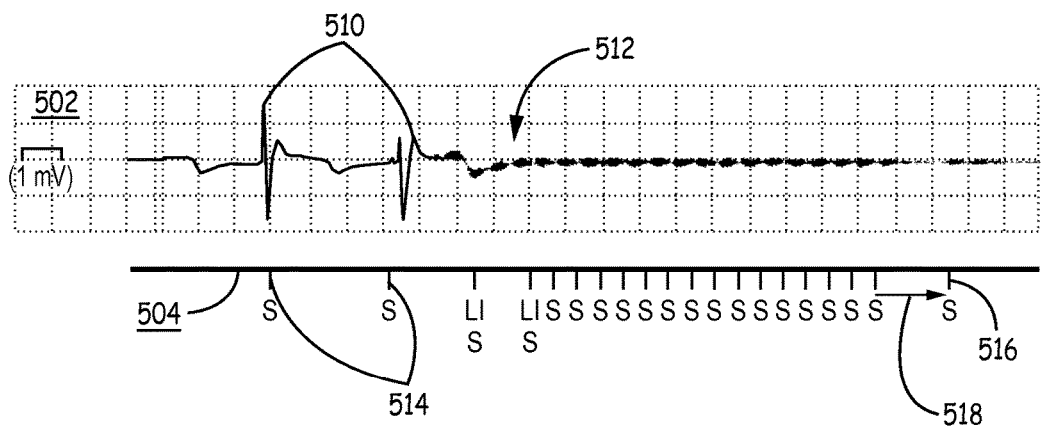

FIG. 8B shows the same cardiac electrical signal 502 shown in FIG. 8A but in this case signal 502 is received by ICD 14 via lead 16 (FIG. 1) and pacing pulses 510 are delivered by another device, e.g., pacemaker 100. ICD 14 may be configured to perform the method described above in conjunction with FIG. 6 for detecting lead issues when pacemaker 100 is present. In this case, the spike detector 114 of ICD 14 will detect the pacing pulses 510 as spikes as shown on spike detection marker channel 504.

In this example, control module 80 is configured to identify lead issue spikes using both EMI exclusion criteria and pacing exclusion criteria, as described in conjunction with FIG. 6. The pacing pulses 510 are detected as spikes 514 by spike detector 114 and are not identified as lead issue spikes by ICD control module 80 because they occur at event intervals that are longer than the maximum lead issue event interval, e.g., the maximum event interval out of the preceding n event intervals less the pacing exclusion interval.

The next two spikes are identified as lead issue spikes because they occur at event intervals longer than the minimum lead issue event interval, e.g., longer than the applied blanking period plus the EMI exclusion interval and shorter than the currently stored maximum event interval less the pacing exclusion interval. All subsequent spikes shown, however, do meet the lead issue spike detection criteria. The maximum event interval is less than a TDI and/or the spike detect signal is within the applied blanking period plus the EMI exclusion interval.

The last spike is detected as a lead issue spike in FIG. 8A because it meets the EMI exclusion criteria and the pacing exclusion criteria are not applied when another therapy delivery device is not present in the patient. The last detected spike 516 in FIG. 8B, however, is not detected as a lead issue spike because it occurs at an event interval 518 that is longer than the maximum lead issue event interval. A maximum event interval determined from three (or other predetermined number) preceding event intervals is relatively short due to the short S-S intervals associated with EMI 512. If the maximum lead issue even interval is set based on the currently stored maximum event interval less the pacing exclusion interval, event interval 518 exceeds this maximum. As such, spike 516 is not identified as a lead issue spike.

The additional pacing exclusion criteria employed by ICD 14 when pacemaker 100 is present may result in occasional undersensing of lead issue spikes. As indicated previously, however, the criteria for detecting a lead issue, e.g., a predetermined frequency of lead issue spikes, may be satisfied with an acceptable level of sensitivity even when some lead issue spikes are not identified. In this way, over detection of a lead issue is avoided when another therapy delivery device is present.

Figure 9A:
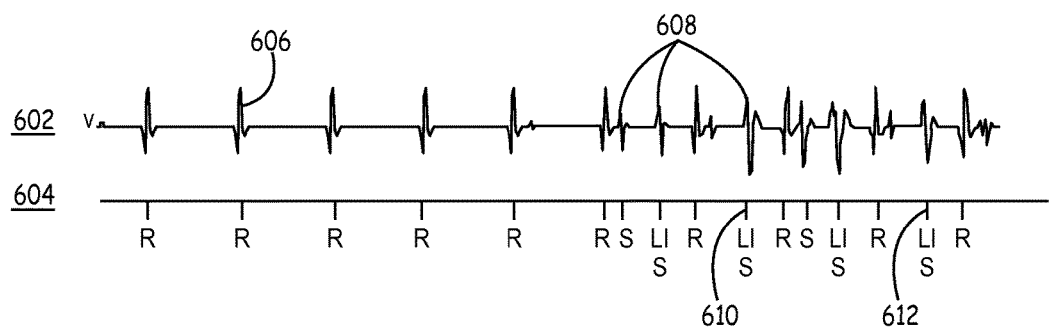
FIGS. 9A and 9B show an example cardiac electrical signal and cardiac event signals and detected spikes caused by a lead issue.

FIG. 9A is a cardiac electrical signal 602 received by an IMD via electrodes carried by a medical electrical lead coupled to the IMD and event signals 604 identifying ventricular sensed events (R) and detected spikes, identified as lead issue spikes and labeled "LIS" or not identified as lead issue spikes and labeled "S." In this example, the cardiac electrical signal 602 includes R-waves 606 and noise spikes 608 due to a lead issue, e.g. an insulation breach of the lead body. The R-waves 606 are properly sensed by the cardiac event detector 120 of sensing channel 101 (FIG. 3), and R-sensed event signals are passed to the control module 80. Spike detector 114 detects spikes 608 caused by the lead issue and passes spike detect signals to the control module 80.

In this example, the spike detect signals are analyzed by control module 80 by determining event intervals as described in conjunction with the flow chart of FIG. 5. The IMD receiving the electrical signal 602 may be ICD 214 configured to deliver pacing therapy and detect a lead issue using EMI exclusion criteria when no other therapy delivery device is present, i.e., without requiring pacing exclusion criteria. Each event interval ending with a spike detect signal is compared to an applied blanking period plus an EMI exclusion interval by control module 80. Each detected spike ending an event interval that is longer than the minimum lead issue event interval is identified as a lead issue spike and will advance the lead issue counter included in control module 80 for detecting the lead issue. The minimum lead issue event interval is set to the applied post-sense blanking period plus the EMI exclusion interval, e.g., 120 ms post-sense blanking plus 20 ms.

One spike detection marker labeled "S" occurs at an event interval after the preceding sensed R-wave that is within the EMI exclusion interval after the post-sense blanking period. This spike may be an underdetected lead issue spike, however, the majority of the lead issue spikes are identified and will lead to a lead issue detection.

Figure 9B:
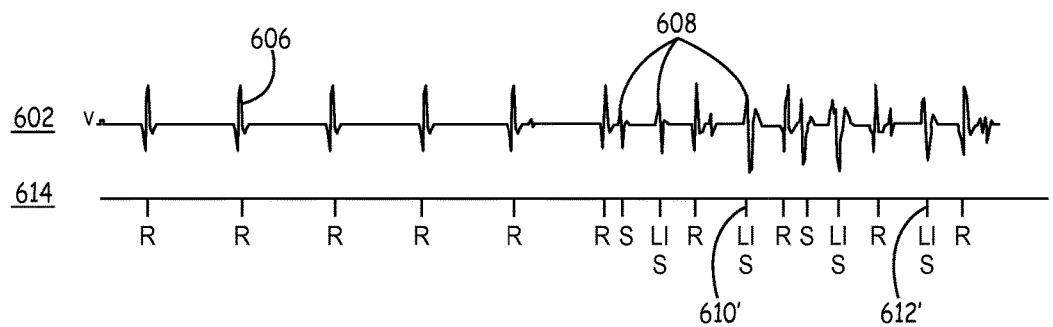

FIG. 9B shows the same cardiac electrical signal 602 including R-waves and signal spikes 608 caused by a lead issue. In this example, the signal 602 is received by ICD 14 when another therapy delivery device, such as pacemaker 100, is present in the patient. The control module 80 applies the EMI exclusion criteria and the pacing exclusion criteria to the event signals 614 received from sensing channel 101 for identifying lead issue spikes. Each spike detect signal ending an event interval that is greater than the applied blanking period plus the EMI exclusion interval and less than a currently stored maximum event interval less a pacing exclusion interval is identified as a lead issue spike.

In this example, the lead issue spikes 610 and 612 in FIG. 9A that occur at event intervals longer than the minimum lead issue event interval are not identified as lead issue spikes 610' and 612' in FIG. 9B. Spikes 610' and 612' occur at an event interval longer than the currently stored maximum event interval less the pacing exclusion that is applied by control module 80 of ICD 14 when another therapy delivery device is present. A spike occurring at an event interval that approaches the maximum event interval may be caused by a pacing pulse delivered by pacemaker 100.

Figure 10:
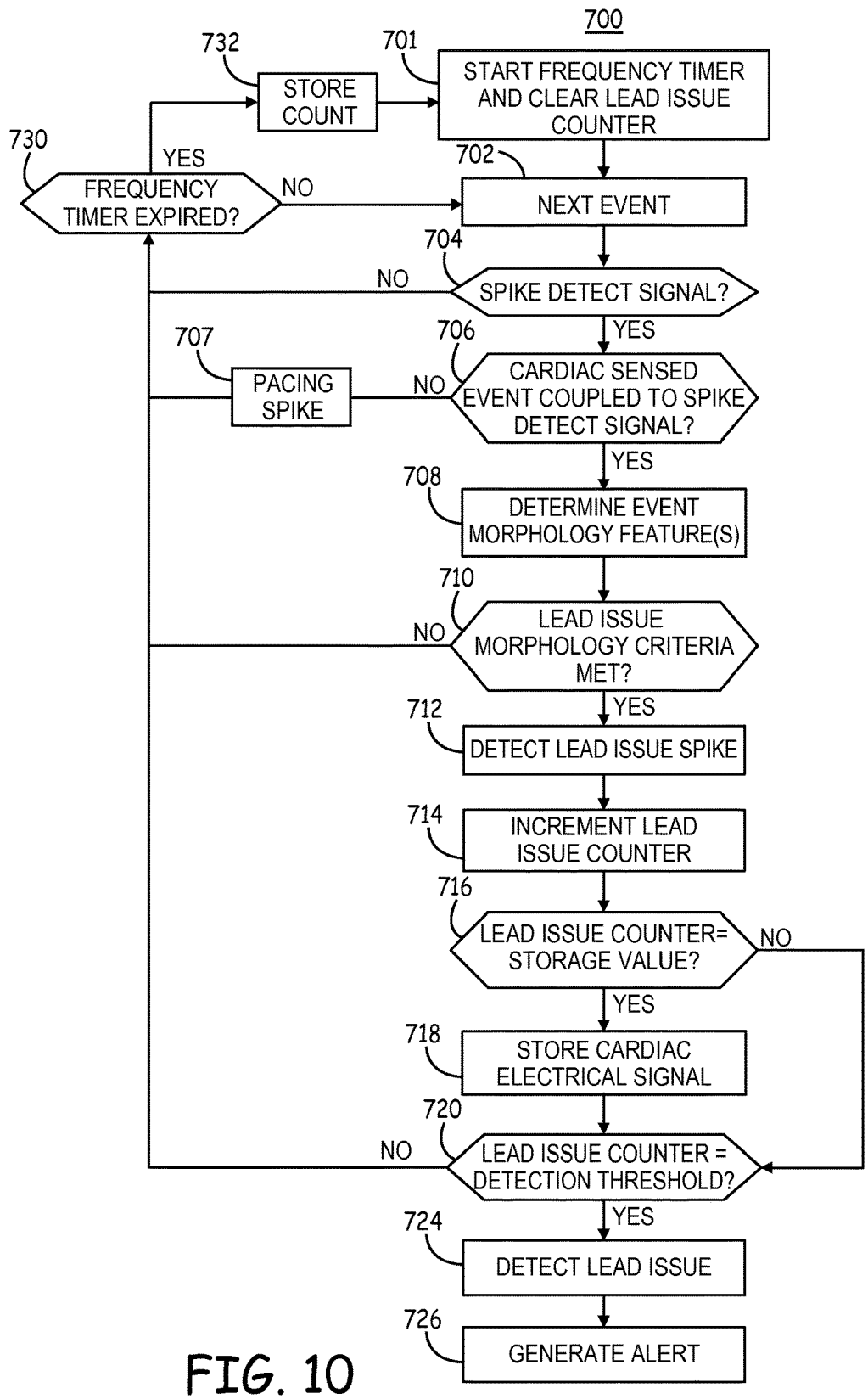
FIG. 10 is a flow chart of a method for detecting a lead issue according to another example.

FIG. 10 is a flow chart 700 of a method for detecting a lead issue according to another example. Referring again to FIG. 3, sensing channel 101 may include spike removal module 110 that is configured to hold a signal value in response to a control signal from blanking control 112 to remove a signal spike from the electrical signal received from decimator 108. Since the most frequently expected signal spikes are expected to be pacing pulses delivered by pacemaker 100 when sensing channel 101 is implemented in ICD 14 (FIG. 1), the spike removal module 110 is optimally configured to remove a signal spike having the characteristics and morphology of a signal spike caused by a pacing pulse. Pacing pulses have a signal amplitude and signal width within a known maximum amplitude and width range and a known signal shape, typically biphasic pulses. As such, spike removal module 110 is configured to effectively remove a pacing pulse spike so that it is not detected as a sensed event by cardiac event detector 120.

Since spike removal module 110 is designed to remove or substantially diminish pacing pulse spikes, which may occur on a very frequent basis, spike removal module 110 may not be optimally configured to remove other types of spikes, particularly lead issue spikes. For example, the spike blanking period may be set to extend for a maximum expected pacing spike width. A lead issue spike may have a signal width that is wider (longer in duration) than a pacing pulse and may therefore extend beyond the spike blanking period. As such, the output of spike removal module 110 received by cardiac event detector 120 and ECG digital filter 122 may include at least a portion of a lead issue spike that is not fully removed or blanked from the ECG signal and does not remain below a cardiac event detection threshold. Cardiac event detector 120 may produce a sensed event signal immediately after the spike blanking period when a portion of a lead issue spike signal remains in the cardiac electrical signal received by cardiac event detector 120. A cardiac sensed event signal within a short interval after the spike blanking period applied by spike removal module 110 or closely coupled in time to the spike detect signal is therefore evidence of a lead issue spike.

In the method of flow chart 700, control module 80 initializes a frequency timer and lead issue counter at block 701 as described previously herein. Upon receiving the next event signal at block 702, control module 80 determines if the event is a spike detect signal at block 704. If so, control module 80 determines if a cardiac sensed event signal is received within a lead issue coupling interval after the spike detection signal at block 706. A lead issue coupling interval may be set to the spike blanking period plus a nominal value, e.g., +20 ms or +40 mf. A closely coupled cardiac sensed event signal may be detected at block 706 when an S-R event interval is less than the lead issue coupling interval.

If a closely coupled cardiac sensed event signal is not received, the detected spike is not identified as a lead issue spike. The spike may be identified as a pacing spike at block 707 since the spike signal has been effectively removed or blanked by spike removal module 110 and is not detected by cardiac event detector 120. If the frequency timer has not yet expired at block 730, the process returns to block 702 to wait for the next event signal.

If a cardiac sensed event signal is received immediately following and closely coupled to the spike detection signal, the spike may be a lead issue spike that is still present in the signal. The spike may be immediately identified as a lead issue spike at block 712, and the lead issue counter may be incremented at block 714. In this case, blocks 708 and 710 would not be present. In other examples, control module 80 may perform a morphology analysis in response to receiving a cardiac sensed event signal closely coupled to a preceding spike detect signal.

Figure 11:
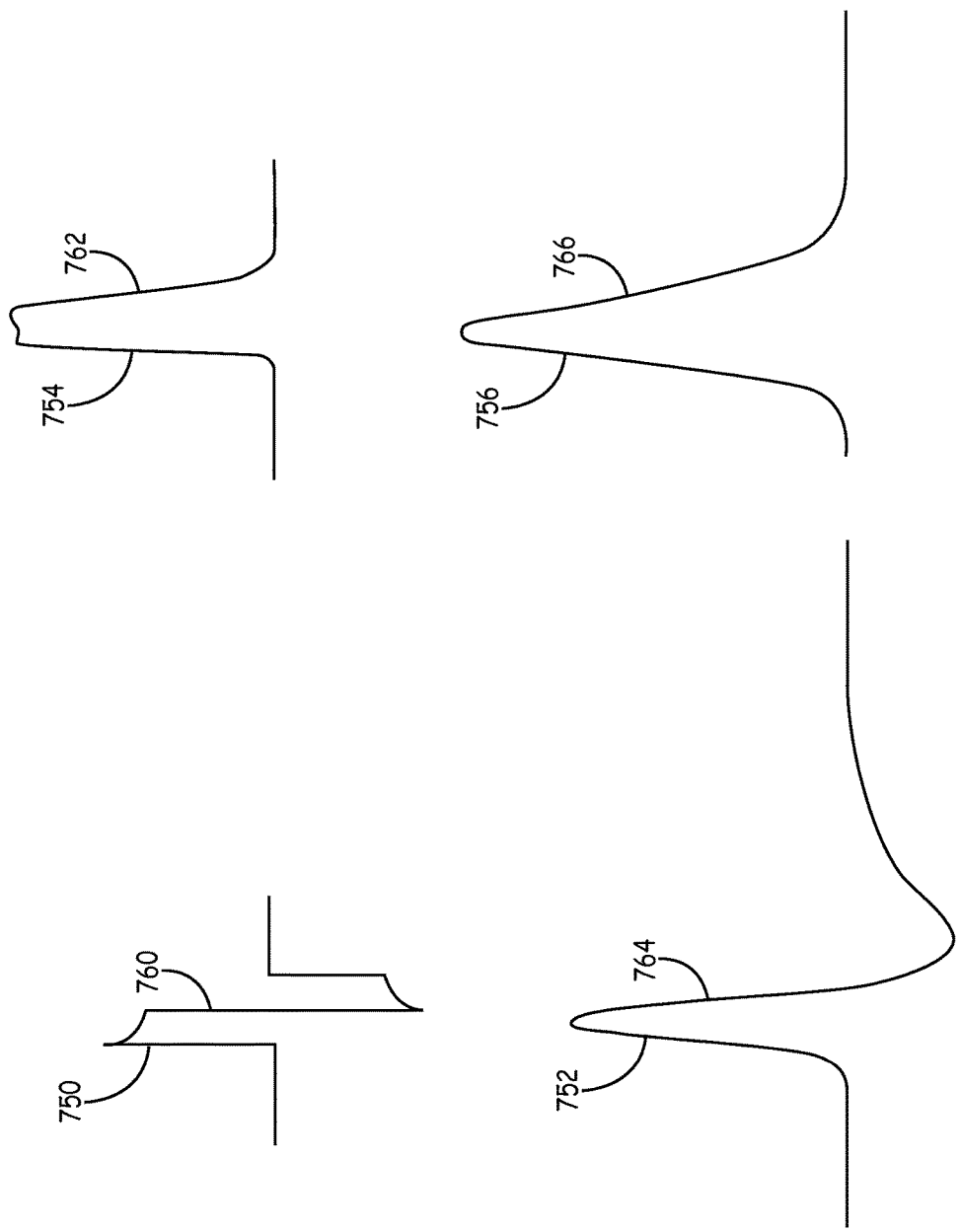
FIG. 11 is a conceptual diagram of a biphasic pacing pulse that may be delivered by a pacemaker and a lead issue noise spike that may appear on a raw cardiac electrical signal received by a sensing channel.

FIG. 11 is a conceptual diagram of a biphasic pacing pulse 750 that may be delivered by pacemaker 100 and a lead issue noise spike 754 that may appear on a raw cardiac electrical signal received by sensing channel 101. As shown in FIG. 11, a pacing pulse is typically a biphasic pulse 750 that produces a biphasic spike signal 752 in the output of the prefilter and preamplifier 102 of sensing channel 101. A lead issue spike 754 is typically a monophasic, substantially rectangular pulse, which may have a step change in amplitude, and produces a monophasic spike signal 756 in the output of prefilter and preamplifier 102.

A common lead issue spike 754 has a post-peak, descending slope 762 that is distinctly less than the sharp polarity change 760 of the biphasic pacing pulse 760. The monophasic signal spike 756 due to a lead issue may be discriminated from a pacing spike signal 752 based on a lower slope of the post-peak descending portion 766 compared to the post-peak descending portion 764 of the pacing spike signal 752. Other distinguishing morphology features of a typical pacing spike 752 and a typical lead issue spike 756 in a blanked or non-blanked ECG/EGM signal provided by sensing channel 101 may be characterized for establishing and defining morphology-based lead issue spike detection criteria. The distinguishing morphology features and therefore the established lead issue spike detection criteria may vary between particular implementations of sensing channel 101 depending on the particular filtering, amplification and other signal processing properties of the particular sensing channel, electrode orientation and other factors.

Returning to flow chart 700, in examples that include blocks 708 and 710 for performing event morphology analysis in making a lead issue spike determination, control module 80 may analyze the morphology of the spike signal in the blanked ECG and/or non-blanked ECG that is concurrent with the cardiac sensed event signal found to be closely coupled to a preceding spike detect signal in order to verify that the spike signal is a lead issue spike and not a pacing spike. Control module 80 may determine one or more morphology features at block 708 from the blanked ECG/EGM signal received from digital filter 122 and/or from the non-blanked ECG/EGM signal received from decimator 108. For example, control module 80 may determine if the spike signal is a monophasic signal (or confirm that it is not a biphasic signal) and/or determine if the descending slope is greater than an established threshold. Additionally or alternatively, control module 80 may determine one or more peak amplitudes, signal widths, slopes, or other features for determining whether the coupled spike detect and sensed event signals are caused by a lead issue spike.

For example, at block 708, the maximum positive peak amplitude and the maximum negative peak amplitude may be determined and compared to lead issue morphology criteria at block 710 that have been established to distinguish a monophasic spike from a biphasic spike. In other examples, the post-peak descending portion of the spike signal may be determined and compared to established criteria to distinguish between a pacing spike and a lead issue spike.

If lead issue morphology criteria are not met at block 710, the process returns to block 730. If the lead issue morphology criteria are met at block 710, a lead issue spike is detected at block 712. The lead issue counter is increased at block 714. The lead issue counter is compared to multiple storage values at block 716 for storing the cardiac electrical signal including the spike signal at block 718 when one of the storage values is met. The lead issue counter is compared to lead issue detection criteria at block 720 to detect a lead issue at block 724 when the current counter value reaches the detection threshold or when a combination of the current counter value and one or more previously stored lead issue counts obtained during preceding frequency time intervals meet the lead issue detection criteria. An alert is generated at block 726 if a lead issue is detected.

If the lead issue detection criteria are not satisfied and the frequency timer has not expired, as determined at block 730, the process returns to block 702 to wait for the next event. If the frequency timer has expired at block 730, the value of the lead issue counter may be stored at block 732 if it is to be used in combination with later lead issue counts for determining if the lead issue detection criteria are satisfied. Storing the count value may be optional in examples that compare only a current lead issue count to lead issue detection criteria, in which case block 732 may be omitted. The frequency timer and the lead issue counter are reset at block 701.

Either or both of the techniques of FIG. 10 for comparing a lead issue coupling interval to an S-R event interval and performing morphology analysis of a spike signal for identifying a lead issue spike may performed alone or in combination with any of the other techniques disclosed herein for identifying lead issue spikes. For example, a lead issue spike may be identified when the event interval ending with the lead issue spike is longer than a minimum lead issue event interval, shorter than a maximum lead issue event interval, is not followed by a closely coupled cardiac sensed event signal, and the spike signal meets lead issue morphology criteria. One or any combination of these criteria may be applied in various examples.

Figure 12:
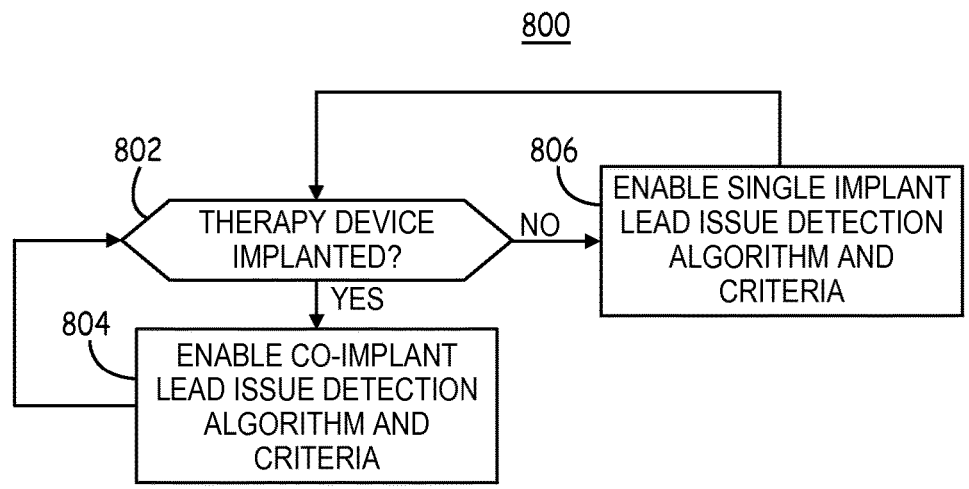
FIG. 12 is a flow chart of a method for selecting a lead issue detection algorithm based on the presence or absence of another functional therapy delivery device in (or on) the patient.

FIG. 12 is a flow chart 800 of a method for selecting a lead issue detection algorithm based on the presence or absence of another functional therapy delivery device in (or on) the patient. At block 802, control module 80 determines if a second implantable (or wearable) device that is capable of delivering electrical stimulation therapy is present in (or on) the patient. The control module 80 may recognize the presence of another therapy delivery device upon receipt of a communication signal by telemetry module 88, either from external device 40 or directly from the therapy delivery device, such as pacemaker 100. In other examples, control module 80 detects the presence of another therapy delivery device automatically by detecting trains of electrical stimulation pulses. Trains of electrical stimulation pulses may be detected using the methods generally disclosed in the above-incorporated '947 patent application for detecting pacing trains.

Control module 80 is configured to adjust the criteria used to identify received spike detect signals as lead issue spikes, and/or adjust lead issue detection criteria, based on whether another therapy delivery device is determined to be present. For example, if another therapy delivery device is determined to be present and functional (e.g., has not reached battery end of life or otherwise had therapy delivery capabilities disabled), control module 80 enables a co-implant lead issue detection algorithm and lead issue detection criteria at block 804, such as the method for detecting a lead issue as shown by flow chart 300 of FIG. 6. The co-implant lead issue detection criteria includes criteria for rejecting spike detect signals caused by electrical stimulation pulses delivered by the other therapy delivery device, such as bradycardia pacing pulses or ATP pulses, as not being lead issue spikes. For example, event intervals ending with a spike detect signal may be required to be less than a maximum lead issue event interval as described above in conjunction with FIG. 6 in order for the spike detect signal to be counted as a lead-issue spike. Other methods that may be enabled in the co-implant lead issue detection algorithm at block 804 are described below in conjunction with FIG. 13.

The lead issue detection algorithm and/or criteria may be modified at block 804 based on the type of therapy delivery device identified to be present at block 802 and/or based on the therapy delivery control parameters programmed into the therapy delivery device. For example, maximum and/or minimum lead issue event intervals may be adjusted based on expected maximum or minimum intervals that might be used to deliver electrical stimulation pulses by the therapy delivery device.

If another therapy delivery device is not determined to be present at block 802, the control module 80 enables a single implant lead issue detection algorithm and associated lead issue detection criteria at block 806. For example, the method shown by flow chart 260 of FIG. 5 may be enabled at block 806. In this case, spikes detected by spike detector 114 will not be pacing spikes or other electrical stimulation spikes caused by therapy delivered by another implanted device. Accordingly, lead issue detection criteria may include criteria for rejecting other types of noise, such as EMI, from being detected as lead issue spikes. In some examples, a minimum lead issue event interval is used to reject spike detect signals that occur at an event interval less than the minimum lead issue event interval since a spike occurring at a short event interval could be a leading edge spike of an episode of EMI. Other techniques for rejecting spike detect signals that may be a leading edge spike of an episode of EMI that may be included in the single implant lead issue detection algorithm are described below in conjunction with FIG. 13.

Control module 80 may be configured to switch back and forth between the co-implant and single implant detection algorithms as needed in response to determining whether another therapy delivery device is present in the patient at block 802. For instance, if the co-implant algorithm and detection criteria are enabled at block 804 and the other therapy delivery device is explanted or reaches end-of-life (and is no longer functional), the implanted ICD 14 (or 214) may determine that the other therapy delivery device is no longer present or at least no longer actively delivering therapy at block 802. This determination may be made at block 802 by receiving a communication signal via telemetry module 88 from external device 40 or by an absence of pacing train detection using the methods disclosed in the '947 application for a predetermined period of time, e.g., several days, weeks or months. In response to determining that the other therapy delivery device is no longer present, the control module 80 switches to the single implant algorithm and detection criteria at block 806.

Figure 13:
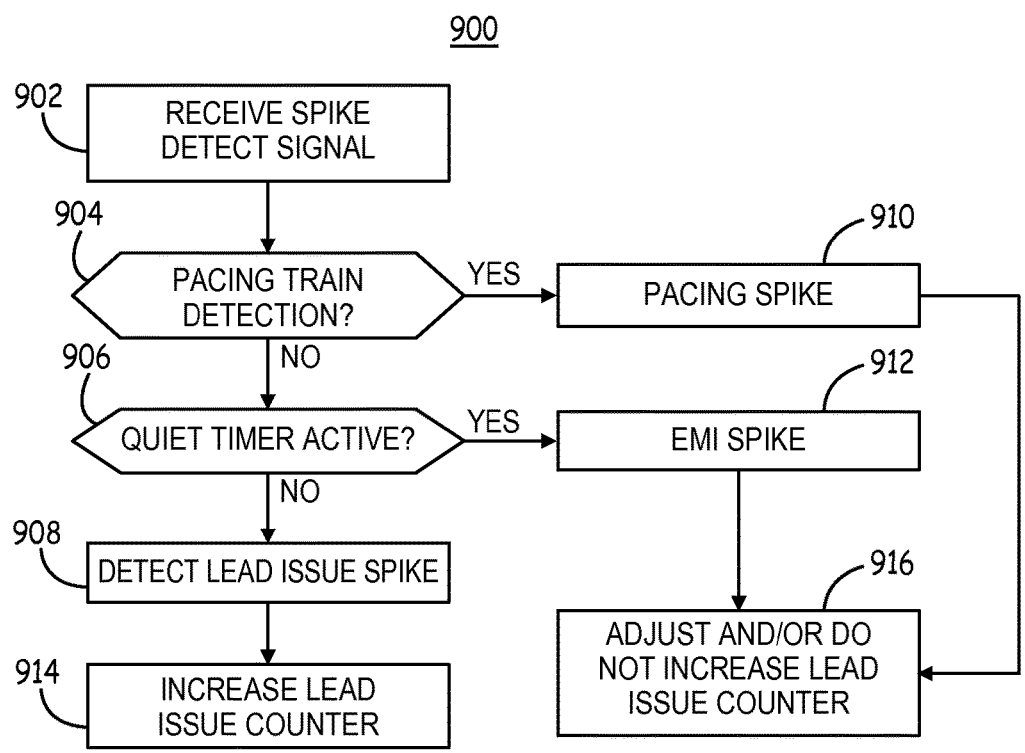
FIG. 13 is a flow chart of a method for identifying spike detect signals that are likely to be lead issue spikes according to another example.

FIG. 13 is a flow chart 900 of a method for identifying spike detect signals that are likely to be lead issue spikes according to another example. At block 902, control module 80 receives a spike detect signal from sensing channel 101. At block 904, control module 80 determines whether the spike detect signal is identified as a pacing spike that is part of a pacing train. Pacing train detection may be performed according to the methods generally disclosed in the above-incorporated '947 application. Briefly, control module 80 may determine cycle lengths between a predetermined number of consecutive spike detect signals and estimate a pacing train cycle length. The estimated pacing train cycle length is compared to one or more cycle length thresholds that correspond to expected pacing intervals used during bradycardia pacing and/or ATP by the other therapy delivery device, e.g., pacemaker 100. A first shortest cycle length threshold may be used to reject EMI, e.g., 40 ms. A second cycle length threshold longer than the first cycle length threshold may be a maximum cycle length expected if the spike detect signals are ATP, e.g., 330 ms. Other criteria may be used to detect a pacing train such as the regularity of the cycle lengths, consistency of the detected spike amplitudes, consistency of the detected spike slew rates, consistency of the detected spike polarities, and/or a maximum duration of a pacing train that is ATP A third threshold may be applied that is a minimum expected bradycardia pacing interval. A predetermined number of spike detect signals, e.g., at least three spike detect signals, occurring regularly at cycle lengths longer than the third threshold may be identified as a bradycardia pacing pulse train. These and other criteria that may be used in detecting trains of pacing pulses that are likely to be ATP or bradycardia pacing are described in the incorporated '947 patent application. If the spike detect signal received at block 902, along with one or more preceding spike detect signals meet criteria for detecting a pacing train at block 904, the spike detect signal is identified as a pacing spike at block 910 and rejected as being a lead issue spike. The pacing spike is not counted by the lead issue counter at block 916.

If a pacing train detection is made at block 904, the preceding spike detect signals that satisfied the pacing cycle length and any other criteria used to detect the pacing train may have been counted previously by the lead issue counter, prior to the pacing train detection criteria becoming satisfied at block 904. In this case, the lead issue counter may be adjusted at block 916 by decreasing the count for each preceding spike detect signal that was counted as a lead issue spike but is now identified as part of a pacing train. To illustrate, if a pacing train detection is made at block 904 on the third spike detect signal of an 8-pulse ATP sequence, the two pulses preceding the third spike detect signal may have been previously counted as lead issue spikes. The lead issue counter may be decreased by two at block 916 and the current, third spike detect signal is not counted. Each of the subsequent five pulses will be identified as the pacing train and will not be counted by lead issue counter at block 916.

If a pacing train is not detected at block 904, the control module 80 may check the status of a quiet timer included in spike detector 114 at block 906. If the quiet timer is active, the spike detect signal is identified as a leading edge spike of an episode of EMI at block 912 and is not counted as a lead issue spike at block 916. The quiet timer may be included in spike detector 114 to prevent spike detector 114 from repeatedly producing spike detect signals during an episode of EMI. For example, upon the onset of EMI, a spike detect signal may be produced at the leading edge of the EMI episode. The quiet timer may be enabled to be active for a predetermined quiet time interval, e.g., at least 10 ms or up to and including 40 ms, to prevent another spike detect signal from being produced if another spike is detected during the quiet time interval.

For example, if 16 Hz EMI is present in the rectified cardiac electrical signal received by spike detector 114, a spike detect signal could be generated as often as every 33 ms without the quiet timer. If 60 Hz EMI is present in the rectified cardiac electrical signal, a spike detect signal could be generated as often as every 8 ms. The quiet timer may be activated by a spike detect signal to prevent another spike detect signal from being produced when a spike is detected within the quiet time interval. The quiet time interval duration is selected to include the cycle time(s) of EMI occurring at one or more frequencies. The quiet time interval is 10 ms in one example to exclude 60 Hz EMI. The quiet time interval is 40 ms in another example to exclude EMI occurring at 16 Hz or higher.

The quiet timer may be re-activated if the spike detector 114 detects another spike during the first quiet time interval. The quiet timer may continue to be re-activated to remain active until the EMI disappears, e.g., no spike is detected during a quiet time interval, or up to a maximum quiet time duration. The quiet timer included in spike detector 114 and its operation to prevent spike detector 114 from producing a series of spike detect signals during EMI may correspond to the quiet timer described in the incorporated '947 patent application.

When a spike detect signal is received at block 902 and a pacing train detection is not being made at block 904, the control module 80 may monitor the status of the quiet timer at block 906. If the quiet timer is re-activated after the first quiet time interval, due to another spike being detected during the first quiet time interval (but no spike detect signal produced), the spike detect signal received at block 902 is likely to be a leading edge spike of an episode of EMI. The spike detect signal is identified as an EMI spike at block 912 in response to the re-activating of the quiet timer for at least one more quiet time intervals. The spike detect signal may be rejected and not counted as a lead issue spike when the quiet timer is re-activated a required number of times.

Identifying the received spike detect signal as a lead issue spike may be withheld if the quiet timer is re-activated for at least one quiet time interval at block 906 (after the first quiet time interval). Monitoring of the quiet timer may continue until the quiet timer is not re-activated or until a threshold number of quiet time intervals have occurred. If the quiet timer remains active at block 906 for a required number of quiet time intervals, control module 80 may reject the received spike detect signal as not being a lead issue spike. The control module 80 may identify the received spike detect signal as the leading edge of an episode of EMI at block 912 if the quiet timer is re-activated for at least two quiet time intervals, at least three quiet time intervals or another threshold number of quiet time intervals. The lead issue counter is not increased at block 916 when the received spike detect signal is identified as an EMI spike.

If the quiet timer is not re-activated at least once after the first quiet time interval at block 906, the spike detect signal received at block 902 is detected as a lead issue spike at block 908. As indicated above, in some examples, the quiet timer may be re-activated up to a threshold number of times, e.g., up to two times, up to three times, or another predetermined threshold number of re-activations, and the received spike detect signal may still be classified as a lead issue spike. As long as the quiet timer does not remain active at block 906 for more than the threshold number of quiet time intervals, the received spike detect signal is identified as a lead issue spike at block 908. The lead issue counter is increased at block 914.

Lead issue detection criteria may be applied to the lead issue count to detect a lead issue by control module 80 as generally described above in conjunction with FIGS. 5 and 6. For example, control module 80 may compare the lead counter value to a lead issue detection threshold for detecting a lead issue. In other examples, the lead counter and a frequency timer may be used to track the frequency of lead issue spikes over one or more frequency time intervals as described above in conjunction with FIGS. 5 and 6 for applying lead issue detection criteria.

All or a portion of the method shown by flow chart 900 may be enabled in the co-implant lead issue detection algorithm at block 804 of FIG. 12. If control module 80 determines that another therapy delivery device is not present or active in the patient, control module 80 may enable the single implant lead issue detection algorithm and criteria at block 806 of FIG. 12 by disabling the pacing train detection block 904. If another therapy delivery device is not present, the control module 80 may enable the single implant lead issue detection algorithm to include monitoring of the quiet timer as described in conjunction with block 906 for detecting a received spike detect signal as a lead issue spike if the quiet timer is not re-activated after the first quiet time interval.

Any of these methods for rejecting spike detect signals as being pacing train spikes or leading edge EMI episode spikes described in relation to FIG. 13 may be used in combination with or substituted for lead issue spike detection criteria described above in conjunction with flow chart 260 of FIG. 5 and/or flow chart 300 of FIG. 6. For example, when a quiet timer is included in spike detector 114 and is configured to be re-activated when a spike is detected during a quiet time interval, control module 80 may monitor the quiet timer status after a spike detect signal is received instead of or in addition to comparing the event interval ending on the spike detect signal to a minimum lead issue event time interval.

When control module 80 is configured to detect trains of pacing pulses based on analysis of spike detect signal cycle lengths, control module 80 may reject spike detect signals identified as part of a detected pacing train in addition to or instead of requiring the event interval ending with the received spike detect signal to be less than a maximum lead issue event interval in order to detect a lead issue spike. In another modification, when control module 80 is configured to detect a pacing train that is likely to be ATP based on an analysis of spike detect signal cycle lengths, control module 80 may reject spike detect signals identified as ATP in addition to or alternatively to comparing the event interval metric to a TDI at block 308. These and other modifications may be made to the flow charts presented herein by combining or substituting the various methods disclosed for rejecting spike detect signals that are likely to be EMI or pacing spikes to provide lead issue detection with high sensitivity and specificity based on spike detect signals received from sensing channel 101 and lead issue detection criteria.

Thus, various examples of medical device apparatus and associated methods have been described for detecting medical electrical lead issues using spike detect signals received from a sensing channel of a medical device. One of ordinary skill in the art will appreciate that various modifications may be made to the described embodiments without departing from the scope of the following claims.

The invention claimed is:

1. An implantable cardiac device comprising:
   a sensing module electrically coupled to one or more electrodes carried by a medical electrical lead coupled to the implantable medical device, the sensing module including:
      a cardiac event detector configured to receive a cardiac electrical signal sensed via at least one of the electrodes carried by the medical electrical lead coupled to the implantable medical device, detect cardiac event signals from the cardiac electrical signal, and produce a cardiac sensed event signal for each of the detected cardiac event signals; and
      a spike detector distinct from the cardiac event detector and configured to receive the cardiac electrical signal, detect non-physiological spikes in the cardiac electrical signal, and produce a spike detect signal for each of the detected non-physiological spikes; and
   a control module electrically coupled to the sensing module, the control module being configured to:
      receive event signals comprising the cardiac sensed event signals and the spike detect signals from the sensing module;
      in response to receiving each of the spike detect signals, determine an event interval defined by the respective spike detect signal and a most recent preceding event signal;
      identify one or more of the received spike detect signals as lead issue spikes based on at least one of the determined event intervals;
      detect a lead issue of the medical electrical lead when a threshold number of spike detect signals are identified as lead issue spikes; and
      generate an alert in response to the lead issue being detected.

2. The device of claim 1, wherein the control module is further configured to establish a minimum lead issue event interval; and
   identify the received spike detect signal as a lead issue spike when a determined event interval ending with the received spike detect signal is longer than the minimum lead issue event interval.

3. The device of claim 2, wherein:
   the sensing module is configured to apply at least one of a first blanking period upon detecting a cardiac event by the cardiac event detector and a second blanking period upon detecting a non-physiological spike by the spike detector;
   the control module is configured to establish the minimum lead issue event interval as an applied one of the first blanking period and the second blanking period plus a predefined electromagnetic interference exclusion interval.

4. The device of claim 1, wherein the control module is further configured to determine an event interval metric from the determined event intervals; and withhold identifying the received spike detect signal as a lead issue spike when the event interval metric is less than a tachycardia detection interval.

5. The device of claim 1, wherein the control module is further configured to:
   determine if an event interval starting with the received spike detect signal and ending on one of the received cardiac sensed event signals is less than a lead issue coupling interval; and
   identify the received spike detect signal as a lead issue spike when the event interval ending on the received cardiac sensed event signal is less than the lead issue coupling time interval.

6. The device of claim 1, wherein the control module is further configured to identify the received spike detect signal as a lead issue spike by:
   determining a morphology feature of a cardiac electrical signal spike associated with the received spike detect signal;
   comparing the morphology feature to lead issue spike detection criteria; and
   identifying the received spike detect signal as a lead issue spike when the lead issue spike detection criteria are satisfied.

7. The device of claim 6, wherein the control module is configured to determine the morphology feature by at least one of determining a descending slope of the cardiac electrical signal spike and determining whether the cardiac electrical signal spike is monophasic.

8. The device of claim 1, wherein the control module is configured to:
   detect a train of pacing pulses in response to a plurality of the determined event intervals; and
   reject one or more of the received spike detect signals as being a lead issue spike in response to detecting the train of pacing pulses.

9. The device of claim 1, wherein:
   the sensing module further comprises a quiet timer, the sensing module further configured to:
      activate the quiet timer for a first quiet time interval in response to producing the spike detect signal,
      withhold producing a next spike detect signal during the first quiet time interval;
      re-activate the quiet timer for a second quiet time interval in response to detecting a spike during the first quiet time interval; and
   the control module is configured to:
      monitor the quiet timer in response to receiving the spike detect signal, and
      withhold identifying the received spike detect signal as a lead issue spike when the quiet timer is re-activated for at least the second quiet time interval.

10. The device of claim 1, wherein the control module is further configured to:
   determine whether a therapy delivery device that is configured to deliver an electrical stimulation therapy is present in the patient; and
   adjust the identifying of the one or more of the received spike detect signals as lead issue spikes based on whether the therapy delivery device is present.

11. The device of claim 1, wherein the medical electrical lead comprises an extravascular implantable medical lead carrying one or more extravascular electrodes that are not on or within the heart of the patient, the device further comprising a therapy delivery module coupled to the control module and configured to deliver electrical shocks to a patient's heart under the control of the control module via at least a portion of the one or more extravascular electrodes carried by the extravascular medical electrical lead.

12. An implantable cardiac device comprising:
   a sensing module electrically coupled to one or more electrodes carried by a medical electrical lead coupled to the implantable medical device, the sensing module including:
      a cardiac event detector configured to receive a cardiac electrical signal sensed via at least one of the electrodes carried by the medical electrical lead coupled to the implantable medical device, detect cardiac event signals from the cardiac electrical signal, and produce a cardiac sensed event signal for each of the detected cardiac event signals; and
      a spike detector configured to receive the cardiac electrical signal, detect non-physiological spikes in the cardiac electrical signal, and produce a spike detect signal for each of the detected non-physiological spikes; and
   a control module electrically coupled to the sensing module, the control module being configured to:
      receive the cardiac sensed event signals and the spike detect signals from the sensing module;
      determine event intervals defined by consecutive ones of the received cardiac sensed event signals and the received spike detect signals;
      identify one or more of the received spike detect signals as lead issue spikes based on at least one of the determined event intervals;
      detect a lead issue of the medical electrical lead when a threshold number of spike detect signals are identified as lead issue spikes; and
      generate an alert in response to the lead issue being detected wherein the control module is further configured to:
   establish a maximum lead issue event interval;
   determine the event intervals by determining at least one event interval ending with one of the received spike detect signals;
   compare the event interval ending with the received spike detect signal to the maximum lead issue event interval; and
   identify the received spike detect signal as a lead issue spike when the event interval ending with the received spike detect signal is less than the maximum lead issue event interval.

13. The device of claim 12, wherein the control module is configured to establish the maximum lead issue event interval by determining a minimum expected pacing interval at which a pacing pulse is expected to be delivered by another medical device.

14. The device of claim 12, wherein the control module is configured to establish the maximum lead issue event interval by:
   determining an event interval metric from the determined event intervals; and
   subtracting a maximum expected pacing cycle change from the event interval metric.

15. A method of identifying a lead issue of a medical electrical lead comprising:
   receiving a cardiac electrical signal by a sensing module of an implantable medical device via electrodes carried by the medical electrical lead coupled to the implantable medical device, detecting cardiac event signals from the cardiac electrical signal by a cardiac event detector of the sensing module;
producing a cardiac sensed event signal for each of the detected cardiac event signals,
detecting non-physiological spikes in the cardiac electrical signal by a spike detector of the sensing module, the spike detector being distinct from the cardiac event detector;
producing a spike detect signal for each of the detected non-physiological spikes;
receiving event signals by a control module of the implantable medical device, the event signals comprising the cardiac sensed event signals and the spike detect signals produced by the sensing module;
in response to receiving each of the spike detect signals, determining an event interval defined by the respective spike detect signals and a most recent preceding event signal;
identifying one or more of the received spike detect signals as lead issue spikes based on at least one of the determined event intervals;
detecting a lead issue of the medical electrical lead when a threshold number of the spike detect signals are identified as lead issue spikes; and
generating an alert in response to detecting the lead issue.

16. The method of claim 15, further comprising:
establishing a minimum lead issue event interval;
determining an event interval ending with the received spike detect signal; and
identifying the received spike detect signal as the lead issue spike when the event interval ending with the received spike detect signal is longer than the minimum lead issue event interval.

17. The method of claim 16, further comprising:
applying at least one of a first blanking period upon detecting a cardiac event by the cardiac event detector and a second blanking period upon detecting a non-physiological spike by the spike detector; and
establishing the minimum lead issue event interval as an applied one of the first blanking period and the second blanking period plus a predefined electromagnetic interference exclusion interval.

18. The method of claim 15, further comprising:
determining an event interval metric from the determined event intervals; and
withholding identifying the received spike detect signal as a lead issue spike when the event interval metric is less than a tachycardia detection interval.

19. The method of claim 15, further comprising:
determining if an event interval starting with a received spike detect signal and ending on a received cardiac sensed event signal is less than a lead issue coupling interval; and
identify the received spike detect signal as a lead issue spike when the event interval ending on the received cardiac sensed event signal is less than the lead issue coupling time interval.

20. The method of claim 15, wherein identifying the received spike detect signal as a lead issue spike further comprises:
determining a morphology feature of a cardiac electrical signal spike associated with the received spike detect signal;
comparing the morphology feature to lead issue spike detection criteria; and
identifying the received spike detect signal as a lead issue spike when the lead issue spike detection criteria are satisfied.

21. The method of claim 20, wherein determining the morphology feature comprises at least one of determining a descending slope of the cardiac electrical signal spike and determining whether the cardiac electrical signal spike is monophasic.

22. The method of claim 15, further comprising:
detecting a train of pacing pulses in response to a plurality of the determined event intervals; and
rejecting one or more of the received spike detect signals as being a lead issue spike in response to detecting the train of pacing pulses.

23. The method of claim 15, further comprising:
activating a quiet timer included in the sensing module for a first quiet time interval in response to producing the spike detect signal,
withholding producing a next spike detect signal during the first quiet time interval;
re-activating the quiet timer for a second quiet time interval in response to detecting a spike during the first quiet time interval;
monitoring the quiet timer by the control module in response to receiving the spike detect signal from the sensing module, and
withholding identifying the received spike detect signal as being a lead issue spike in response to the quiet timer being re-activated for at least the second quiet time interval.

24. The method of claim 15, further comprising:
determining whether a therapy delivery device that is configured to deliver an electrical stimulation therapy is present in the patient; and
adjusting the identifying of the one or more of the received spike detect signals as lead issue spikes based on whether the therapy delivery device is present.

25. A method of identifying a lead issue of a medical electrical lead comprising:
receiving a cardiac electrical signal by a sensing module of an implantable medical device via electrodes carried by the medical electrical lead coupled to the implantable medical device,
detecting cardiac event signals from the cardiac electrical signal by a cardiac event detector of the sensing module;
producing a cardiac sensed event signal for each of the detected cardiac event signals,
detecting non-physiological spikes in the cardiac electrical signal by a spike detector of the sensing module;
producing a spike detect signal for each of the detected non-physiological spikes;
establishing a maximum lead issue event interval;
receiving the cardiac sensed event signals and the spike detect signals produced by the sensing module by a control module of the implantable medical device;
determining event intervals defined by consecutive ones of the received cardiac sensed event signals and the received spike detect signals, wherein determining the event intervals comprises determining at least one event interval ending with one of the received spike detect signals;
identifying one or more of the received spike detect signals as lead issue spikes based on at least one of the determined event intervals by comparing the event interval ending with the received spike detect signal to the maximum lead issue event interval and identifying the received spike detect signal as a lead issue spike when the event interval ending with the received spike detect signal is less than the maximum lead issue event interval;

detecting a lead issue of the medical electrical lead when a threshold number of the spike detect signals are identified as lead issue spikes; and generating an alert in response to detecting the lead issue.

26. The method of claim 25, wherein establishing the maximum lead issue event interval comprises determining a minimum expected pacing interval at which a pacing pulse is expected to be delivered by another medical device.

27. The method of claim 25, wherein establishing the maximum lead issue event interval comprises:
   determining an event interval metric from the determined event intervals; and
   subtracting a maximum expected pacing cycle change from the event interval metric.

28. A non-transitory computer readable storage medium comprising instructions which when executed by a control module of an implantable medical device cause the implantable medical device to:

determine event intervals defined by cardiac sensed event signals and spike detect signals produced by a cardiac event detector and a spike detector distinct from the cardiac event detector, respectively, of a sensing module of the implantable medical device, the sensing module configured to receive a cardiac electrical signal via electrodes carried by a medical electrical lead coupled to the implantable medical device and detect cardiac event signals and non-physiological spikes from the cardiac electrical signal;

identify one or more of the spike detect signals as lead issue spikes based on at least one of the determined event intervals defined by a received spike detect signal and a most recent preceding event signal;

detect a lead issue of the medical electrical lead when a threshold number of the spike detect signals are identified as lead issue spikes; and generate an alert in response to detecting the lead issue.

* * * * *